(12) United States Patent
Mastalerz et al.

(10) Patent No.: US 7,619,083 B2
(45) Date of Patent: Nov. 17, 2009

(54) INTERMEDIATES USEFUL IN PREPARING CERTAIN PYRROLOTRIAZINE COMPOUNDS AND PROCESS FOR MAKING SUCH INTERMEDIATES

(75) Inventors: Harold Mastalerz, Guilford, CT (US); Guifen Zhang, Wallingford, CT (US)

(73) Assignee: Bristol-Myers Squibb Company, Princeton, NJ (US)

( * ) Notice: Subject to any disclaimer, the term of this patent is extended or adjusted under 35 U.S.C. 154(b) by 143 days.

(21) Appl. No.: 11/426,707

(22) Filed: Jun. 27, 2006

(65) Prior Publication Data

US 2007/0015760 A1    Jan. 18, 2007

Related U.S. Application Data

(60) Provisional application No. 60/696,215, filed on Jul. 1, 2005, provisional application No. 60/748,024, filed on Dec. 7, 2005.

(51) Int. Cl.
*C07D 487/04* (2006.01)
*A61K 31/53* (2006.01)
*A61P 19/02* (2006.01)
*A61P 35/00* (2006.01)

(52) U.S. Cl. .................. 544/183; 514/241

(58) Field of Classification Search .............. 544/183
See application file for complete search history.

(56) References Cited

U.S. PATENT DOCUMENTS

| | | | |
|---|---|---|---|
| 6,670,357 B2 | 12/2003 | Leftheris et al. | |
| 6,982,265 B1 | 1/2006 | Hunt et al. | |
| 7,030,118 B2 | 4/2006 | Lombardo et al. | |
| 7,034,151 B2 | 4/2006 | Chen et al. | |
| 7,112,675 B2 | 9/2006 | Hunt et al. | |
| 7,442,700 B2* | 10/2008 | Mastalerz et al. | 514/243 |
| 2005/0288289 A1 | 12/2005 | Crispino et al. | |
| 2006/0004006 A1 | 1/2006 | Borzilleri et al. | |
| 2006/0084650 A1* | 4/2006 | Dong et al. | 514/243 |

OTHER PUBLICATIONS

Lamartina et al., Journal of Heterocyclic Chemistry 19(6), 1381-1384 (1982).
Migliara et al., Journal of Heterocyclic Chemistry 16(5), 833-834 (1979).

* cited by examiner

*Primary Examiner*—Venkataraman Balasubramanian
(74) *Attorney, Agent, or Firm*—Elliott Korsen

(57) ABSTRACT

The invention relates to 2,4-dichloropyrrolo[1,2-f][1,2,4]triazines, which are intermediates useful in preparing at least one 2,4-disubstituted pyrrolotriazine compound, and at least one method for making such intermediates.

18 Claims, No Drawings

INTERMEDIATES USEFUL IN PREPARING CERTAIN PYRROLOTRIAZINE COMPOUNDS AND PROCESS FOR MAKING SUCH INTERMEDIATES

CROSS-REFERENCE TO RELATED APPLICATIONS

This application claims the benefit of U.S. Provisional Application No. 60/696,215, filed Jul. 1, 2005 and U.S. Provisional Application No. 60/748,024, filed Dec. 7, 2005, the contents of which are both hereby incorporated herein by reference.

FIELD OF THE INVENTION

Described herein is at least one 2,4-dichloropyrrolo[1,2-f][1,2,4]triazine, which is an intermediates useful in preparing at least one 2,4-disubstituted pyrrolotriazine compound, and at least one method for making such intermediates.

BACKGROUND OF THE INVENTION

Hyperproliferative diseases, such as, for example, cancer are generally characterized by uncontrolled cellular proliferation and/or disruption in programmed cell death. Uncontrolled cellular proliferation is often caused by genetic damage to cellular pathways responsible for regulating cellular functions, such as, for example, metabolism, cell cycle progression, cell adhesion, vascular function, apoptosis, and angiogenesis. As a result, one approach utilized in treating hyperproliferative diseases has involved targeting at least one protein involved in regulating cellular functions.

The protein kinase(s) (PK(s)) are a class of proteins that have been identified as playing an important role in regulating cellular functions. Indeed, many diseases are associated with abnormal cellular responses triggered by PK-mediated events. Such diseases include, but are not limited to, for example, autoimmune diseases, bone diseases, inflammatory diseases/disorders, metabolic diseases, neurological and neurodegenerative diseases, cancer, cardiovascular diseases, allergies and asthma, Alzheimer's disease, and hormone related diseases.

The PKs are a large and diverse group of enzymes that can be divided into groups based on the particular amino acids (serine/threonine, tyrosine, lysine, and histidine) targeted by each PK. For example, receptor and non-receptor tyrosine kinases target tyrosine, whereas cyclin dependent kinases (CDKs) and mitogen activated protein kinases (MAPKs) target both tyrosine and serine/threonine.

Exemplary PKs include, but are not limited to, for example, receptor tyrosine kinases (RTKs); non-receptor tyrosine kinases or cellular tyrosine kinases (CTKs); serine/threonine kinases (STKs); cyclin dependent kinases (CDKs); and mitogen-activated protein kinases (MAPKs).

Exemplary RTKs include, but are not limited to, for example, type III RTKs, such as, for example, Flt3; "HER" RTKs, such as, for example, epithelial growth factor receptor (EGFR), HER2, HER3, and HER4; C-MET; insulin receptor (IR); insulin-like growth factor 1 receptor (IGF-1R) and its ligands IGF-1 and IGF-2; insulin receptor related receptor (IRR); platelet derived growth factor receptors (PDGFRs), such as, for example, PDGFRα, PDGFRβ, CSFIR, c-kit, and c-fms; fetus liver kinases (flks), such as, for example, kinase insert domain-receptor fetal liver kinase-1 (KDR/FLK-1, VEGF-R2), flk-1R, flk-4, and fms-like tyrosine kinase 1 (flt-1); fibroblast growth factor (FGF) receptors, such as, for example, FGFR1, FGFR2, FGFR3, and FGFR4 and FGF ligands, such as, for example, FGF 1, FGF2, FGF3, FGF4, FGF5, FGF6, and FGF7; vascular endothelial growth factor receptors(VEGFRs), such as, for example, VEGFR1, VEGFR2, and VEGFR3; Tie receptors, such as for example, Tie2; and Trk receptors, such as, for example, TrkA, TrkB, and TrkC. For a more detailed discussion of RTKs, see Plowman et al., KN&P, 7 (6):334-339 (1994).

Exemplary CTKs include, but are not limited to, for example, Src kinases, such as, for example, Src, Yes, Fyn, Lyn, Lck, Blk, Hck, Fgr, and Yrk; Frk kinases; Btk kinases; Csk kinases; Abl kinases; ZAP70 kinases; Fes kinases; Fps kinases; Fak kinases; Jak kinases; Ack kinases; and Kak kinases. For a more detailed discussion of known CTKs, see Bolen, *Oncogene*, 8:2025-2031 (1993).

Exemplary STKs include, but are not limited to, for example, p90 ribosomal S6 kinases (RSKs), such as, for example, RSK1/p90Rsk, RSK2, RSK3, and RSK4; checkpoint protein kinases, such as, for example, CHK1 and CHK2; AURORA kinases, such as, for example, aurora-A, aurora-B, and aurora-C; and Glycogen synthase kinase 3 (GSK3).

Exemplary CDKs include, but are not limited to, for example, CDK1; CDK2; CDK4; CDK5; CDK6; CDK 7; and cell division control 2 proteins (CDC2);

Exemplary MAPKs include, but are not limited to, for example, MAPK 1 (ERK); MAPK3; MAPK7; MAPK 8 (JNK1); MAPK 14 (p38α); MAPK 10; JNK 3 αprotein kinase; stress-activated protein kinase JNK 2; and MAPK 14.

In view of the link between PK-related cellular activities and a wide variety of human disorders, including, for example, cancer, and the discovery that certain pyrrolotriazine-containing compounds exhibit inhibitory activity of at least one PK, such pyrrolotriazine-containing compounds were found to be useful in treating conditions associated with abnormal PK activity.

SUMMARY OF THE INVENTION

Described herein are compounds of formula VI,

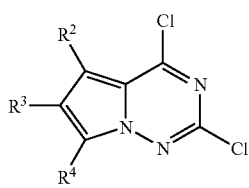

VI or a pharmaceutically acceptable salt thereof, wherein:

$R^2$, $R^3$, and $R^4$ are independently selected from H, alkyl, substituted alkyl, hydroxy, alkoxy, halogen, haloalkyl, haloalkoxy, alkanoyl, substituted alkanoyl, amino, substituted amino, aminoalkyl, substituted aminoalkyl, alkylamino, substituted alkylamino, amide, substituted amide, carbamate, ureido, cyano, sulfonamide, substituted sulfonamide, alkylsulfone, cycloalkyl, substituted cycloalkyl, nitro, thio, thioalkyl, alkylthio, disubstituted amino, alkylsulfonyl, alkylsulfinyl, carboxy, alkoxycarbonyl, alkylcarbonyloxy, carbamoyl, —$NR^5(C═O)R^6$, alkenyl, substituted alkenyl, alkynyl, substituted alkynyl, and alkylcarbonyl;

$R^5$ is H, lower alkyl, or substituted lower alkyl; and
$R^6$ is H, alkyl, substituted alkyl, alkoxy, amino alkyl, substituted amino alkyl, alkylamino, substituted alkylamino, aryl, or substituted aryl.

Further described herein is at least one process for preparing at least one formula VI compound as defined hereinabove, or a pharmaceutically acceptable salt thereof comprising contacting at least one compound of formula V,

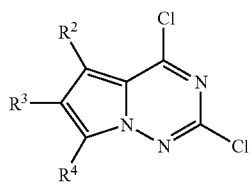

or a pharmaceutically acceptable salt thereof, wherein $R^2$, $R^3$, and $R^4$ are as defined hereinabove, with at least one chlorinating agent to form a mixture, and heating the mixture to form at least one compound of formula VI, or a pharmaceutically acceptable salt thereof.

Even further described herein is a process for preparing at least one compound in accordance with formula VI:

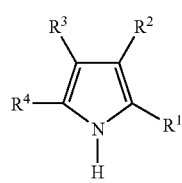

or a pharmaceutically acceptable salt thereof, wherein $R^2$, $R^3$, and $R^4$ are as defined hereinabove, by contacting at least one compound of formula I,

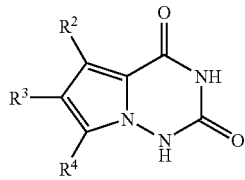

wherein $R^1$ is CHO or CN and $R^2$, $R^3$, and $R^4$ are as defined hereinabove; with at least one aminating agent in the presence of at least one base to form at least one compound of formula II,

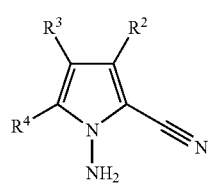

wherein $R^2$, $R^3$, and $R^4$ are as defined hereinabove; converting at least one compound of formula II to at least one compound of formula III,

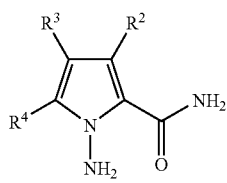

wherein $R^2$, $R^3$, and $R^4$ are as defined hereinabove; contacting the formula III compound with at least one reagent in the presence of at least one base and at least one solvent to form at least one compound of formula V,

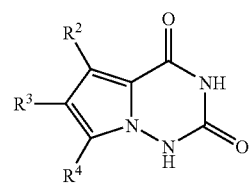

or a pharmaceutically acceptable salt thereof, wherein $R^2$, $R^3$, and $R^4$ are as defined hereinabove; contacting the formula V compound, or pharmaceutically acceptable salt thereof, with at least one chlorinating agent to form a mixture, and heating the mixture to form at least one compound of formula VI, or a pharmaceutically acceptable salt thereof.

DETAILED DESCRIPTION OF THE INVENTION

The features and advantages of the invention may be more readily understood by those of ordinary skill in the art upon reading the following detailed description. It is to be appreciated that certain features of the invention that are, for clarity reasons, described above and below in the context of separate embodiments, may also be combined to form a single embodiment. Conversely, various features of the invention that are, for brevity reasons, described in the context of a single embodiment, may also be combined so as to form sub-combinations thereof.

Unless specifically stated otherwise herein, references made in the singular may also include the plural. For example, "a" and "an" may refer to either one, or one or more.

All numbers expressing quantities of ingredients, properties such as molecular weight, reaction conditions, and so forth that are preceded by the word "about" are to be understood as only approximations so that slight variations above and below the stated number may be used to achieve substantially the same results as the stated number. Accordingly, unless indicated to the contrary, numerical parameters preceded by the word "about" are approximations that may vary depending upon the desired properties sought to be obtained by the invention. At the very least, and not as an attempt to limit the application of the doctrine of equivalents to the scope of the claims, each numerical parameter should at least be construed in light of the number of reported significant digits and by applying ordinary rounding techniques.

It is to be understood that each of the variously stated ranges is intended to be continuous so as to include each numerical parameter between the stated minimum and maximum value of each range. It is to be further understood that, while not intending to limit the applicability of the doctrine of equivalents to the scope of the claims, each numerical parameter should at least be construed in a manner consistent with the reported number of significant digits for each numerical parameter and by applying ordinary rounding techniques. It is to be even further understood that, while not intending to limit the applicability of the doctrine of equivalents to the scope of the claims, even though a number may be contained within a numerical range wherein at least one of the minimum and maximum numbers of the range is or is not preceded by the word "about", each numerical value contained within the range may or may not be preceded by the word "about". For Example, a range of about 1 to about 10 includes about 1, about 2, 2, about 3, 3, about 4, 4, about 5, 5, about 6, 6, about 7, 7, about 8, 8, about 9, 9, and about 10; a range of about 1.1 to about 3.2 includes about 1.1, about 1.2, 1.2, about 1.3, 1.3, about 1.4, 1.4, about 1.5, 1.5, about 1.6, 1.6, about 1.7, 1.7, about 1.8, 1.8, about 1.9, 1.9, about 2.0, 2.0, about 2.1, 2.1, about 2.2, 2.2, about 2.3, 2.3, about 2.4, 2.4, about 2.5, 2.5, about 2.6, 2.6, about 2.7, 2.7, about 2.8, 2.8, about 2.9, 2.9, about 3.0, 3.0, about 3.1, 3.1, and about 3.2; and a range of about 1 to 4 includes about 1, 2, about 2, 3, about 3, and 4.

Further, when an amount, concentration, or other value or parameter is given as a list of upper values and lower values, such listings are intended to include all ranges formed by pairing any upper value with any lower value, regardless of whether ranges are separately disclosed.

Unless otherwise indicated, any heteroatom with unsatisfied valences is assumed to have hydrogen atoms sufficient to satisfy the valences.

The definitions set forth herein take precedence over definitions set forth in any patent, patent application, and/or patent application publication incorporated herein by reference.

Throughout the specification, groups and substituents thereof may be chosen by one skilled in the field to provide stable moieties and compounds.

Embodiments identified herein as exemplary or preferred are intended to be illustrative and not limiting.

Definitions of terms used in describing the invention are set forth hereinbelow. Unless otherwise indicated, the initial definition provided for a group or term applies each time such group or term is used individually or as part of another group.

The terms "alkyl" and "alk" refer to a straight chain or branched chain saturated hydrocarbon radical containing from 1 to 12 carbon atoms and preferably from 1 to 6 carbon atoms. Exemplary "alkyl" and/or "alk" groups include, but are not limited to, for example, methyl, ethyl, propyl, isopropyl, 1-methylpropyl, n-butyl, t-butyl, isobutyl, pentyl, hexyl, isohexyl, heptyl, 4,4-dimethylpentyl, diethylpentyl, octyl, 2,2,4-trimethylpentyl, nonyl, decyl, undecyl, and dodecyl.

The term "substituted alkyl" refers to an alkyl group substituted with at least one substituent at any available and substitutable position. Exemplary substituents include, but are not limited to, for example, hydrogen, alkyl, hydroxy (—OH), alkoxy, halogen, haloalkyl, haloalkoxy, oxo, aryloxy, arylalkyl, arylalkyloxy, alkanoyl, substituted alkanoyl, alkanoyloxy, amino, aminoalkyl, substituted aminoalkyl, alkylamino, substituted alkylamino, hydroxyalkyl, disubstituted amino, amide, substituted amide, carbamate, substituted carbamate, ureido, cyano, sulfonamide, substituted sulfonamide, alkylsulfone, heterocycloalkyl, substituted heterocycloalkyl, cycloalkyl, substituted cycloalkyl, cycloalkylalkyl, cycloalkylalkoxy, nitro, thio, thioalkyl, alkylthio, alkylsulfonyl, alkylsulfinyl, carboxy, alkoxycarbonyl, alkylcarbonyloxy, carbamoyl, —NR$^5$(C=O)R$^6$, alkenyl, substituted alkenyl, alkynyl, substituted alkynyl, aryl, substituted aryl, heteroaryl, substituted heteroaryl, heteroaryloxy, arylheteroaryl, arylalkoxycarbonyl, heteroarylalkyl, heteroarylalkoxy, aryloxyalkyl, aryloxyaryl, heterocycle, substituted heterocycle, alkylcarbonyl, heteroalkyl, substituted heteroalkyl, heteroalkenyl, substituted heteroalkenyl, heteroalkynyl, substituted heteroalkynyl, arylamino, arylalkylamino, alkanoylamino, arylamino, arylalkanoylamino, arylthio, arylalkylthio, arylsulfonyl, arylalkylsulfonyl, arylcarbonylamino, and alkylaminocarbonyl.

The term "lower alkyl" refers to an alkyl group containing from 1 to 4 carbon atoms. It is of import to note that although the term "lower alkyl" is encompassed within the definition of "alkyl", the usage of the term "lower alkyl" is not intended to limit the definition of the term "alkyl" either explicitly or implicitly to a straight-or branched-chain saturated hydrocarbon radical containing from 5 to 7 carbon atoms. Exemplary lower alkyl groups include, but are not limited to, for example, methyl; ethyl; propyl; isopropyl; n-butyl; t-butyl; isobutyl; pentyl; and isopentyl The term "substituted lower alkyl" refers to a lower alkyl substituted at any available and substitutable position with at least one alkyl, substituted alkyl, or substituent described above in defining the term "substituted alkyl" as an exemplary alkyl substituent.

The term "aryl" refers to monocyclic or bicyclic aromatic hydrocarbon rings having from 6 to 12 carbon atoms in the ring portion. Exemplary aryl groups include but are not limited to, for example, phenyl; naphthalenyl; biphenyl; and diphenyl groups. When two aromatic rings are present, the aromatic rings of the aryl group may either be joined at a single point (e.g., biphenyl), or be fused (e.g., naphthalenyl). The term "aryl" also includes rings having a second, third, fourth, or fifth ring fused thereto that is a heterocyclo, substituted heterocyclo, heteroaryl, substituted heteroaryl, aryl, substituted aryl, cycloalkyl, or substituted cycloalkyl, provided in such cases the point of attachment is to the aryl portion of the ring system. The term "aryl" further includes rings having a second, third, fourth, or fifth ring attached to the ring or ring system in a spiro fashion, wherein such second, third, fourth, or fifth ring is a heterocyclo, substituted heterocyclo, heteroaryl, substituted heteroaryl, aryl, substituted aryl, cycloalkyl, or substituted cycloalkyl.

The term "substituted aryl" refers to an aryl substituted with at least one substituent at any available and substitutable ring position, or where valence allows on any rings fused or attached thereto. Exemplary substituents include, but are not limited to, for example, hydrogen; alkyl, substituted alkyl, hydroxy (—OH), alkoxy, alkoxyalkyl, alkoxycarbonyl, alkoxyarylthio, halogen, haloalkyl, haloalkoxy, aryl, aryloxy, arylalkyl, arylalkyloxy, alkanoyl, substituted alkanoyl, alkanoylamino, amino, aminoalkyl, substituted aminoalkyl, alkylamino, substituted alkylamino, disubstituted amino, aminocarbonyl, arylamino, arylalkylamino, arylalkoxy, ureido, cyano, sulfonamide, substituted sulfonamide, heterocycloalkyl, substituted heterocycloalkyl, heterocycloalkylalkyl, cycloalkyl, substituted cycloalkyl, cycloalkylalkyl, cycloalkylalkoxy, nitro, thio, thioalkyl, alkylthio, alkylsulfonyl, alkylsulfinyl, carboxy, carboxyalkyl, carboxyalkoxy, alkoxycarbonyl, alkylcarbonyloxy, carbamoyl, alkenyl, substituted alkenyl, alkynyl, substituted alkynyl, arylsulfonylamino, arylalkenyl, aryloxycarbonyl, arylthio, arylthioalkyl, arylalkylthio, sulfonic acid, heteroaryl, substituted heteroaryl, heteroarylthio, heteroaryloxy, heteroarylalkenyl, heteroarylheteroaryl, heteroarylalkylthio, heteroaryloxyalkyl, alkylcarbonyl, aminocarbonylaryl, aminocarbonylalkyl, arylazo, alkoxycarbonylalkoxy, arylcarbonyl, alkylaminocarbonyl, aminoalkylcarbonyl, arylaminocarbonyl, alkylcarbonyloxy, arylcarbonyloxy, alkylcarbonylamino, arylcarbonylamino, arylsulfonyl, heteroarylsulfonyl, heterocycloalkylsulfonyl, arylsulfinyl, arylsulfinylalkyl, and arylsulfonylaminocarbonyl.

The term "substituted phenyl" refers to a phenyl substituted with at least one substituent described above as a "substituted aryl" substituent.

The terms "aryloxy", "arylamino", "arylalkylamino", "arylthio", "arylalkanoylamino", "arylsulfonyl", "arylalkoxy", "arylsulfinyl", "arylheteroaryl", "arylalkylthio", "arylcarbonyl", "arylalkenyl", or "arylalkylsulfonyl" refer to an aryl or substituted aryl bonded to an oxygen; an amino; an alkylamino; a thio; an alkanoylamino; a sulfonyl; an alkoxy; a sulfinyl; a heteroaryl or substituted heteroaryl; an alkylthio; a carbonyl; an alkenyl; or an alkylsulfonyl, respectively The term "arylsulfonylaminocarbonyl" refers to an arylsulfonyl bonded to an aminocarbonyl.

The terms "aryloxyalkyl", "aryloxycarbonyl" or "aryloxyaryl" refer to an aryloxy bonded to an alkyl or substituted alkyl; a carbonyl; or an aryl or substituted aryl, respectively.

The term "arylalkyl" refers to an alkyl or substituted alkyl in which at least one of the hydrogen atoms bonded to at least one of the carbon atoms is replaced with an aryl or substituted aryl. Typical arylalkyls include, but are not limited to, for example, benzyl, 2-phenylethan-1-yl, 2-phenylethen-1-yl, naphthylmethyl, 2-naphthylethan-1-yl, 2-naphthylethen-1-yl, naphthobenzyl, and 2-naphthophenylethan-1-yl.

The term "arylalkyloxy" refers to an arylalkyl bonded through an oxygen linkage (—O—arylalkyl).

The terms "arylthioalkyl" or "arylsulfinylalkyl" refer to an arylthio or an arylsulfinyl, respectively, bonded to an alkyl or substituted alkyl.

The term "heteroaryl" refers to aromatic cyclic groups, such as, for example, 5-to 6-membered monocyclic, 7-to 11-membered bicyclic, or 10-to 16-membered tricyclic ring systems having at least one heteroatom in at least one carbon atom-containing ring. The carbon atom-containing ring may contain 1, 2, 3, or 4 heteroatom(s) selected from nitrogen, oxygen, and/or sulfur. The heteroaryl group may be attached to another moiety at any available point of attachment.

Exemplary monocyclic heteroaryl groups include, but are not limited to, for example, pyrazolyl, imidazolyl, triazolyl, oxazolyl, furyl, thiazolyl, isoxazolyl, thiazolyl, pyridyl

[i.e., 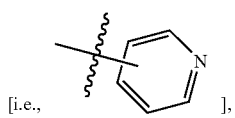 ], pyridazinyl

[i.e., 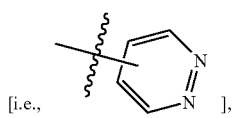 ], pyrimidinyl

[i.e., 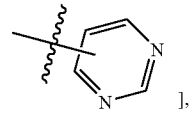 ], pyrazinyl

[i.e., 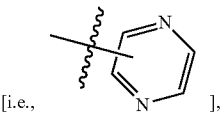 ], and triazinyl. Unless reference is made to a specific point of attachment, e.g., as in pyrid-2-yl, pyridazin-3-yl, it is intended that such heteroaryl groups can be bonded to another moiety at any available point of attachment.

Exemplary bicyclic heteroaryl groups include, but are not limited to, for example, benzothiazolyl, benzoxazolyl, benzoxadiazolyl, benzothienyl, quinolinyl, chromenyl, indolyl, indazolyl, isoquinolinyl, benzimidazolyl, benzopyranyl, benzofuryl, benzofurazanyl, benzopyranyl, cinnolinyl, quinoxalinyl, pyrrolopyridyl, furopyridinyl (such as furo[2,3-c]pyridinyl, furo[3,2-b]pyridinyl] or furo[2,3-b]pyridinyl), and triazinylazepinyl.

The term "substituted heteroaryl" refers to a heteroaryl substituted at any available and substitutable ring position, or where valence allows on any rings fused or attached thereto, with at least one aryl, substituted aryl, or substituent described above in defining the term "substituted aryl" as an exemplary aryl substituent.

The terms "heteroaryloxy", "heteroarylalkenyl", "heteroarylheteroaryl", "heteroarylalkyl", "heteroarylalkoxy", "heteroarylthio", "heteroarylsulfonyl", or "heteroarylalkylthio" refer to a heteroaryl or substituted heteroaryl bonded to an oxygen; an alkenyl or substituted alkenyl; a heteroaryl or substituted heteroaryl; an alkyl or substituted alkyl; an alkoxy; a thio; a sulfonyl; or an alkylthio, respectively.

The term "heteroaryloxyalkyl" refers to a heteroaryloxy bonded to an alkyl or substituted alkyl.

The term "cycloalkyl" refers to a fully saturated or partially unsaturated cyclic hydrocarbon group containing from 1 to 3 rings and 3 to 8 carbons per ring. Exemplary cycloalkyls include, but are not limited to, for example, cyclopropyl, cyclobutyl, cyclopentyl, cyclohexyl, cycloheptyl, cyclobutenyl, cyclopentenyl, and cyclohexenyl. A cycloalkyl ring may have a carbon ring atom replaced with a carbonyl group (C=O). Cycloalkyls include such rings having a second or third ring fused thereto that is a heterocyclo, substituted heterocyclo, heteroaryl, substituted heteroaryl, aryl or substituted aryl, provided that in such cases the point of attachment is to the cycloalkyl portion of the ring system. The term "cycloalkyl" also includes rings having a second or third ring attached to the ring or ring system in a spiro fashion.

The term "substituted cycloalkyl" refers to a cycloalkyl substituted with at least one substitutent, preferably 1 to 4 substituents, more preferably 1 to 2 substituents, at any available point of attachment on either the cycloalkyl ring, or where valence allows on any rings fused or attached thereto. Exemplary substituents include, but are not limited to, for example, alkyl, substituted alkyl, and the substituents described in defining the term "substituted alkyl" as exemplary alkyl substituents.

Exemplary cycloalkyls include but are not limited to, for example,

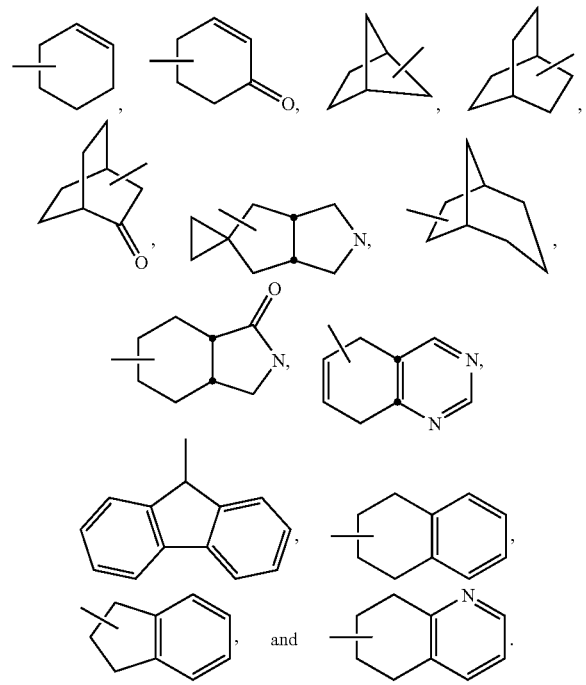

The term "heterocycloalkyl" refers to a saturated or unsaturated cycloalkyl in which one or more carbons (and any associated hydrogen atoms) are independently replaced with at least one heteroatom selected from O and N.

The term "substituted heterocycloalkyl" refers to a heterocycloalkyl substituted at any available and substitutable ring position with at least one alkyl, substituted alkyl, or substituent described above in defining the term "substituted alkyl" as an exemplary alkyl substituent.

The terms "heterocycloalkylalkyl" or "heterocycloalkylsulfonyl" refer to a heterocycloalkyl or substituted heterocycloalkyl bonded to an alkyl or substituted alkyl or a sulfonyl, respectively.

The terms "heterocycle", "heterocyclic", and "heterocyclo" refer to fully saturated or partially or fully unsaturated, aromatic or nonaromatic cyclic groups that are, for example, 4 to 7 membered monocyclic, 7 to 11 membered bicyclic, or 10 to 15 membered tricyclic ring systems that have at least one heteroatom in at least one carbon atom containing ring. Each ring of the heterocycle, heterocyclic, or heterocyclo containing a heteroatom may have 1, 2 or 3 heteroatoms selected from N, O, and S, where the N and/or S heteroatom(s) may optionally be oxidized and the N heteroatom(s) may optionally be quaternized. The heterocycle, heterocyclic, or heterocyclo may be attached to the remainder of the molecule via any available heteroatom or carbon atom. Heterocycle, heterocyclic, or heterocyclo include such rings having a second or third ring fused thereto that is a heterocyclo, substituted heterocyclo, heteroaryl, substituted heteroaryl, aryl, substituted aryl, cycloalkyl, or substituted cycloalkyl, provided in such cases the point of attachment is to the heterocycle, heterocyclic, or heterocyclo portion of the ring system. The terms "heterocycle", "heterocyclic", or "heterocyclol" also include rings having a second or third ring attached to the ring or ring system in a spiro fashion, wherein such second or third ring is a heterocyclo, substituted heterocyclo, heteroaryl, substituted heteroaryl, aryl, substituted aryl, cycloalkyl, or substituted cycloalkyl.

Exemplary monocyclic heterocycles, heterocyclics, or heterocyclos include, but are not limited to, for example, pyrrolidinyl, pyrrolyl, indolyl, pyrazolyl, oxetanyl, pyrazolinyl, imidazolyl, imidazolinyl, imidazolidinyl, oxazolyl, oxazolidinyl, isoxazolinyl, isoxazolyl, thiazolyl, thiadiazolyl, thiazolidinyl, isothiazolyl, isothiazolidinyl, furyl, tetrahydrofuryl, thienyl, oxadiazolyl, piperidinyl, piperazinyl, 2-oxopiperazinyl, 2-oxopiperidinyl, homopiperazinyl, 2-oxohomopiperazinyl, 2-oxopyrrolidinyl, 2-oxazepinyl, azepinyl, 4-piperidonyl, pyridyl, N-oxo-pyridyl, pyrazinyl, pyrimidinyl, pyridazinyl, tetrahydropyranyl, morpholinyl, thiamorpholinyl, thiamorpholinyl sulfoxide, thiamorpholinyl sulfone, 1,3-dioxolane and tetrahydro-1,1-dioxothienyl, dioxanyl, isothiazolidinyl, thietanyl, thiiranyl, triazinyl, and triazolyl.

Exemplary bicyclic heterocycles, heterocyclics, or heterocyclos include, but are not limited to, for example, 2,3-dihydro-2-oxo-1H-indolyl, benzothiazolyl, benzoxazolyl, benzothienyl, quinuclidinyl, quinolinyl, quinolinyl-N-oxide, tetrahydroisoquinolinyl, isoquinolinyl, benzimidazolyl, benzopyranyl, indolizinyl, benzofuryl, chromonyl, coumarinyl, cinnolinyl, quinoxalinyl, indazolyl, pyrrolopyridyl, furopyridinyl (such as furo[2,3-c]pyridinyl, furo[3,1-b]pyridinyl] or furo[2,3-b]pyridinyl), dihydroisoindolyl, dihydroquinazolinyl (such as 3,4-dihydro-4-oxo-quinazolinyl), benzisothiazolyl, benzisoxazolyl, benzodiazinyl, benzofurazanyl, benzothiopyranyl, benzotriazolyl, benzpyrazolyl, dihydrobenzofuryl, dihydrobenzothienyl, dihydrobenzothiopyranyl, dihydrobenzothiopyranyl sulfone, dihydrobenzopyranyl, indolinyl, indazolyl, isochromanyl, isoindolinyl, naphthyridinyl, phthalazinyl, piperonyl, purinyl, pyridopyridyl, quinazolinyl, tetrahydroquinolinyl, thienofuryl, thienopyridyl, and thienothienyl.

The terms "substituted heterocycle", "substituted heterocyclic", or "substituted heterocyclo" refer to a heterocycle, heterocyclic, or heterocyclo, respectively, substituted at any available point of attachment, or where valence allows on any rings fused or attached thereto, with at least one alkyl, substituted alkyl, or substituent described above in defining the term "substituted alkyl" as an exemplary alkyl substituent.

The terms "heteroalkyl", "heteroalkenyl", or "heteroalkynyl" refer to an alkyl, alkenyl, or alkynyl, respectively, in which one or more of the carbon atoms (and any associated hydrogen atoms) are each independently replaced with the same or different heteroatoms. Typical heteroatoms include, but are not limited to, for example, —O—, —S—, —O—O—, —S—S—, —O—S—, —NR$^a$—, =N—N=, —N=N—, —N=N—NR', —PH—, —P(O)$_2$—, —O—P(O)$_2$—, —S(O)—, —S(O)$_2$—, and —SnH$_2$—, wherein R$^a$ is hydrogen, alkyl, substituted alkyl, cycloalkyl, substituted cycloalkyl, aryl, or substituted aryl.

The terms "substituted heteroalkyl", "substituted heteroalkenyl", or "substituted heteroalkynyl" refer to a heteroalkyl, heteroalkenyl, or heteroalkynyl, respectively, substituted with at least one alkyl, substituted alkyl, or substituent described above in defining the term "substituted alkyl" as an exemplary alkyl substituent.

The term "hydroxyalkyl" refers to an —R$^b$OH, wherein R$^b$ is an alkyl or substituted alkyl.

The term "amino" refers to —NH$_2$.

The term "aminoalkyl" refers to an alkyl substituted with an amino having having at least one hydrogen replaced with a group chosen from alkyl, alkenyl, and cycloalkyl. Thus, aminoalkyl refers to the group —R$^c$NR$^d$R$^e$, wherein R$^c$ is an alkyl and $R^d$ and $R^e$ are independently selected from hydrogen, alkyl, alkenyl, and cycloalkyl, provided $R^d$ and $R^e$ are not both hydrogen.

The term "substituted aminoalkyl" refers to an aminoalkyl wherein at least one of the alkyl, alkenyl, or cycloalkyl moieties is substituted with at least one, preferably 1 to 4, more preferably 1 to 2 groups selected from those recited herein as appropriate for the recited moiety. Thus, for example, a substituted aminoalkyl refers to the group —$R^cNR^dR^e$, wherein $R^c$ is an alkyl or substituted alkyl and $R^d$ and $R^e$ are independently selected from H, alkyl, substituted alkyl, alkenyl, substituted alkenyl, cycloalkyl, and substituted cycloalkyl, provided $R^d$ and $R^e$ are not both hydrogen as in that case the group would be amino and not substituted aminoalkyl; and that at least one of $R^c$, $R^d$, or $R^e$ is a substituted moiety.

The term "alkylamino" refers to an amino having at least one hydrogen replaced with a group chosen from alkyl, alkenyl, and cycloalkyl. Thus, alkylamino refers to the group —$NR^fR^g$, wherein $R^f$ and $R^g$ are independently selected form H, alkyl, alkenyl, and cycloalkyl, provided at least one of $R^f$ or $R^g$ is an alkyl.

The term "substituted alkylamino" refers to an alkylamino wherein at least one of the alkyl, alkenyl, or cycloalkyl moieties is substituted with at least one, preferably 1 to 4, more preferably 1 to 2 groups selected from those recited herein as appropriate substituents for the recited moiety. Thus, for example, a substituted alkylamino refers to the group —$NR^fR^g$, wherein $R^f$ and $R^g$ are independently selected form H, alkyl, substituted alkyl, alkenyl, substituted alkenyl, cycloalkyl, and substituted cycloalkyl, provided at least one of $R^f$ or $R^g$ is an alkyl and at least one of $R^f$ or $R^g$ is a substituted moiety.

The term "disubstituted amino" refers to an amino having both hydrogens replaced with a group chosen from alkyl, substituted alkyl, alkenyl, substituted alkenyl, cycloalkyl, and substituted cycloalkyl. Thus, for example, a disubstituted amino refers to the group —$NR^hR^i$, wherein $R^h$ and $R^i$ are independently selected from alkyl, substituted alkyl, alkenyl, substituted alkenyl, cycloalkyl, and substituted cycloalkyl.

The terms "halogen" and "halo" refer to chlorine, bromine, fluorine, and iodine.

The terms "haloalkyl" or "haloalkoxy" refer to an alkyl or substituted alkyl; or an alkoxy, respectively, bonded to a single halogen or multiple halogens. Exemplary haloalkyls containing multiple halogens include, but are not limited to, for example, —$CHCl_2$ and —$CF_3$. Exemplary haloalkoxys containing multiple halogens include, but are not limited to, for example, trifluoromethoxy (—$OCF_3$).

The term "alkoxy" refers to an alkyl, substituted alkyl, alkanoyl, substituted alkanoyl, cycloalkyl or substituted cycloalkyl bonded through an oxygen linkage (—O-alkyl, —O-substituted alkyl, —O-alkanoyl, —O-substituted alkanoyl, —O-cycloalkyl, or —O-substituted cycloalkyl). Exemplary alkoxy groups include, but are not limited to, for example, methoxy, ethoxy, propoxy, isopropoxy, n-butoxy, t-butoxy, isobutoxy, pentoxy, isopentoxy, hexoxy, heptoxy, pentoxy, decanoxy, undecanoxy, and dodecanoxy.

The terms "alkoxyalkyl" or "alkoxyarylthio" refer to an alkyl or substituted alkyl; or an arylthio, respectively, bonded to an alkoxy.

The term "alkenyl" refers to a straight or branched chain hydrocarbon radical containing from 2 to 12 carbon atoms and at least one carbon-carbon double bond. Exemplary alkenyls include, but are not limited to, for example, ethenyl and allyl.

The term "substituted alkenyl" refers to an alkenyl substituted with at least one substituent, preferably 1 to 4 substituents, more preferably 1 to 2 substituents, at any available point of attachment. Exemplary substituents include, but are not limited to, for example, alkyl, substituted alkyl, and the substituents described above in defining the term "substituted alkyl" as exemplary alkyl substituents.

The term "cycloalkenyl" refers to a cyclized alkenyl.

The term "substituted cycloalkenyl" refers to a cyclized substituted alkenyl.

The term "alkanoyl" refers to an alkyl bonded through a carbonyl (i.e. —$C(=O)R^j$, wherein $R^j$ is an alkyl).

The term "substituted alkanoyl" refers to an alkanoyl substituted with at least one substituent, preferably 1 to 4 substituents, more preferably 1 to 2 substituents, at any available point of attachment. Exemplary substituents include, but are not limited to, for example, alkyl, substituted alkyl, and the substituents described above in defining the term "substituted alkyl" as exemplary alkyl substituents.

The terms "alkanoylamino", "arylcarbonylamino", "alkylcarbonylamino", or "arylsulfonylamino" refer to an alkanoyl or substituted alkanoyl; an arylcarbonyl; an alkylcarbonyl; or an arylsulfonyl, respectively, bonded to an amino.

The term "alkanoyloxy" refers to an alkanoyl or substituted alkanoyl bonded to an oxygen.

The term "alkynyl" refers to a straight or branched chain hydrocarbon radical containing from 2 to 12 carbon atoms and at least one carbon-carbon triple bond. Exemplary alkynyls include, but are not limited to, for example, ethynyl; propynyls, such as, for example, prop-1-yn-1-yl and prop-2-yn-1-yl; and butynyls, such as, for example, but-1-yn-1-yl, but-1-yn-3-yl, and but-3-yn-1-yl.

The term "substituted alkynyl" refers to an alkynyl substituted with at least one substituent, preferably 1 to 4 substituents, more preferably 1 to 2 substituents, at any available point of attachment. Exemplary substituents include, but are not limited to, for example, alkyl, substituted alkyl, and the substituents described above in defining the term "substituted alkyl" as exemplary alkyl substituents.

The term "alkylsulfone" refers to —$R^kS(=O)_2R^k$, wherein $R^k$ is an alkyl or substituted alkyl.

The term "oxo" refers to the divalent radical =O.

The term "carbamate" refers to the group —$OC(=O)NH_2$.

The term "amide" refers to the group —$C(=O)NH_2$.

The term "sulfonamide" refers to the group —$SO_2NH_2$.

The terms "substituted amide", "substituted sulfonamide", or "substituted carbamate" refer to an amide, sulfonamide, or carbamate, respectively, having at least one hydrogen replaced with a group chosen from alkyl, substituted alkyl, alkenyl, substituted alkenyl, cycloalkyl, and substituted cycloalkyl.

A substituted amide, for example, refers to the group —$C(=O)NR^mR^n$ wherein $R^m$ and $R^n$ are independently selected from H, alkyl, substituted alkyl, alkenyl, substituted alkenyl, cycloalkyl, and substituted cycloalkyl, provided at least one of $R^m$ or $R^n$ is a substituted moiety.

A substituted sulfonamide, for example, refers to the group —$SO_2NR^oR^p$ wherein $R^o$ and $R^p$ are independently selected from alkyl, substituted alkyl, alkenyl, substituted alkenyl, cycloalkyl, and substituted cycloalkyl, provided at least one of $R^o$ or $R^p$ is a substituted moiety.

A substituted carbamate, for example, refers to the group —$OC(=O)NR^qR^r$ wherein $R^q$ and $R^r$ are independently selected from alkyl, substituted alkyl, alkenyl, substituted alkenyl, cycloalkyl, and substituted cycloalkyl, provided at least one of $R^q$ or $R^r$ is a substituted moiety.

The term "ureido" refers to the group —$NHC(=O)NH_2$.

The term "cyano" refers to the group —CN.

The terms "cycloalkylalkyl" or "cycloalkylalkoxy" refer to a cycloalkyl or substituted cycloalkyl bonded to an alkyl or substituted alkyl; or an alkoxy, respectively.

The term "nitro" refers to the group —N(O)$_2$.

The term "thio" refers to the group —SH.

The term "alkylthio" refers to the group —SR$^s$ where R$^s$ is an alkyl, substituted alkyl, cycloalkyl, or substituted cycloalkyl.

The term "thioalkyl" refers to the group —R$^t$S where R$^t$ is an alkyl, substituted alkyl, cycloalkyl, or substituted cycloalkyl.

The term "alkylsulfonyl" refers to the group —S(=O)$_2$R$^u$ where R$^u$ is an alkyl, substituted alkyl, cycloalkyl, or substituted cycloalkyl.

The term "alkylsulfinyl" refers to the group —S(=O)R$^v$ where R$^v$ is an alkyl, substituted alkyl, cycloalkyl, or substituted cycloalkyl.

The term "carboxy" refers to the group —C(=O)OH.

The terms "carboxyalkoxy" or "alkoxycarbonylalkoxy" refer to a carboxy, or an alkoxycarbonyl, respectively, bonded to an alkoxy.

The term "alkoxycarbonyl" refers to the group —C(=O)OR$^w$ where R$^w$ is an alkyl, substituted alkyl, cycloalkyl, substituted cycloalkyl, aryl, substituted aryl, heteroaryl, or substituted heteroaryl.

The term "arylalkoxycarbonyl" refers to an aryl or substituted aryl bonded to an alkoxycarbonyl.

The terms "alkylcarbonyloxy" or "arylcarbonyloxy" refer to the group —OC(=O)R$^x$, where R$^x$ is an alkyl or substituted alkyl, or an aryl or substituted aryl, respectively.

The term "carbamoyl" refers to the groups —OC(=O)NH$_2$, —OC(=O)NHR$^x$, and/or —OC(=O)NR$^y$R$^z$, wherein R$^y$ and R$^z$ are independently selected from alkyl and substituted alkyl.

The group —NR$^5$(C=O)R$^6$ refers to a group where R$^5$ is selected from hydrogen, lower alkyl and substituted lower alkyl, and R$^6$ is selected from hydrogen, alkyl, substituted alkyl, alkoxy, aminoalkyl, substituted aminoalkyl, alkylamino, substituted alkylamino, aryl and substituted aryl.

The term "carbonyl" refers to a C(=O).

The terms "alkylcarbonyl", "aminocarbonyl", "alkylaminocarbonyl" "aminoalkylcarbonyl", or "arylaminocarbonyl" refer to an alkyl or substituted alkyl; an amino; an alkylamino or substituted alkylamino; an aminoalkyl or substituted aminoalkyl; or an arylamino, respectively, bonded to a carbonyl.

The terms "aminocarbonylaryl" or "aminocarbonylalkyl" refer to an aminocarbonyl bonded to an aryl or substituted aryl; or an alkyl or substituted alkyl, respectively.

The term "sulfonyl" refers to the group S(=O)$_2$.

The term "sulfinyl" refers to an S(=O).

The term "carboxyalkyl" refers to an alkyl or substituted alkyl bonded to a carboxy.

When a functional group is termed "protected", this means an art-recognized protecting group capable of attaching to the particular functional group is attached to such functional group to mitigate, especially preclude, undesired side reactions at the protected site.

The term "salt(s)", as employed herein, denotes acidic and/or basic salts formed with inorganic and/or organic acids and/or bases, and such term, as used herein, further includes zwitterion(s) ("inner salts").

The terms "zwitterion(s)", as employed herein, denote compound(s) containing both a basic moiety, including but not limited to, for example, pyridine and imidazole; and an acidic moiety including but not limited to, for example, a carboxylic acid.

The term "pharmaceutically acceptable", as employed herein, indicates the subject matter being identified as "pharmaceutically acceptable" is suitable and physiologically acceptable for administration to a patient. For example, the term "pharmaceutically acceptable salt(s)" denotes suitable and physiologically acceptable salt(s) for administration to a patient.

Formula V and VI compounds can also form salt(s). As a result, when a compound of formula V and/or VI is referred to herein, such reference includes, unless otherwise indicated, salts thereof. Exemplary salts include, but are not limited to, for example, acidic and/or basic salt(s) formed with inorganic and/or organic acids and bases, and zwitterion(s) ("inner salts"). In one embodiment, compounds of formula V and/or VI form pharmaceutically acceptable salts. In another embodiment, compounds of formula V and/or VI form salts that can, for example, be used in isolating and/or purifying compounds of formula V and/or VI. Salt(s) of formula V and/or VI compounds can be formed by, for example, reacting a formula V and/or VI compound with, for example, an equivalent amount of acid or base in a medium that allows the thusly formed salt to, for example, either precipitate out, or be isolated via lyophilization.

Exemplary acidic salt(s) compounds of Formula V and/or VI can form with inorganic and/or organic acids include, but are not limited to, for example, acetates, such as are formed with acetic or trihaloacetic acid; adipates; alginates; ascorbates; aspartates; benzoates; benzenesulfonates; bisulfates; borates; butyrates; citrates; camphorates; camphorsulfonates; cyclopentanepropionates; digluconates; dodecylsulfates; ethanesulfonates; fumarates; glucoheptanoates; glycerophosphates; hemisulfates; heptanoates; hexanoates; hydrochlorides; hydrobromides; hydroiodides; hydroxyethanesulfonates, such as, for example, 2-hydroxyethanesulfonates; lactates; maleates; methanesulfonates; naphthalenesulfonates, such as, for example, 2-naphthalenesulfonates; nicotinates; nitrates; oxalates; pectinates; persulfates; phenylpropionates, such as, for example, 3-phenylpropionates; phosphates; picrates; pivalates; propionates; salicylates; succinates; sulfates, such as, for example, are formed with sulfuric acid; sulfonates; tartrates; thiocyanates; and toluenesulfonates, such as, for example, tosylates and undecanoates. Such salts can be formed in accordance with methods known to a person of ordinary skill in the art.

Exemplary basic salt(s) that compounds of Formula V and/or VI can form with inorganic and/or organic bases include, but are not limited to, for example, ammonium salts; alkali metal salts, such as, for example, sodium, lithium and potassium salts: alkaline earth metal salts, such as, for example, calcium and magnesium salts; salts formed with organic bases, such as, for example, benzathines, dicyclohexylamines, hydrabamines (such as, for example, N,N-bis (dehydroabietyl) ethylenediamine), N-methyl-D-glucamines, N-methyl-D-glycamides, and t-butyl amines; salts formed with amino acids, such as, for example, arginine and lysine; and salts formed by using agents, such as, for example, lower alkyl halides (e.g. methyl, ethyl, propyl, and butyl chlorides, bromides and iodides), dialkyl sulfates (e.g. dimethyl, diethyl, dibutyl, and diamyl sulfates), long chain halides (e.g. decyl, lauryl, myristyl and stearyl chlorides, bromides and iodides), and aralkyl halides (e.g. benzyl and phenethyl bromides) to quaternize basic nitrogen-containing groups. Such salts can be formed in accordance with methods known to a person of ordinary skill in the art.

All stereoisomer(s) and geometric isomer(s) of the compounds of formula V and/or VI, either in admixture or in pure or substantially pure form are also contemplated herein. Specifically, all enantiomers, tautomers, and diastereomers of the compounds of formula V and/or VI, as well as mixtures, compounds, racemic compounds, racemic mixtures, and racemates produced therefrom are contemplated herein. Even more particularly, all optically active isomers of the compounds of formula V and/or VI, including pure or substantially pure optically active isomers, i.e., optically active isomers substantially free of other isomers.

When a compound containing a single enantiomer of a compound of formula V and/or VI is desired, such compound can be obtained by either resolution of the final product or by stereospecific synthesis from either isomerically pure starting material(s), or any convenient intermediate(s). Resolution of the final product, an intermediate, or a starting material can be effected by any suitable method known in the art, including, for example, physical methods, such as, for example, fractional crystallization, separation or crystallization of diastereomeric derivatives, and separation by chiral column chromatography. Individual optical isomers can be obtained from racemates through, for example, conventional methods, such as, for example, salt formation with an optically active acid followed by crystallization. The chiral centers of compounds in accordance with formula V and/or VI can have the S or R configuration as defined by the IUPAC 1974 Recommendations.

Described herein are compounds of Formula VI,

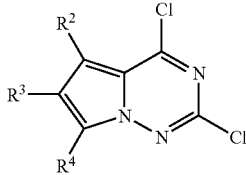

or pharmaceutically acceptable salts thereof, wherein $R^2$, $R^3$, and $R^4$ are as defined hereinabove.

A person of ordinary skill in the art will readily recognize that various $R^2$, $R^3$, and $R^4$ groups identified hereinabove may need to be protected to prevent the group from taking place in reactions occurring elsewhere on the molecule to which the group is attached. Suitable protecting groups include, but are not limited to, for example, protecting groups described in standard textbooks, such as Greene, T. W. et al., *Protective Groups in Organic Synthesis*, Wiley, N.Y. (1999). For example, when an $R^2$, $R^3$, and/or $R^4$ group is an amino, the protecting group can, for example, be a urethane type protective group (which is also referred to as a carbamate protective group) including, but not limited to, for example, arylalkyloxycarbonyl groups, such as, for example, benzyloxycarbonyl; and alkoxycarbonyl groups, such as, for example, methoxycarbonyl, and tert-butoxycarbonyl.

In one embodiment, $R^2$, $R^3$, and $R^4$ are hydrogen.

Further described herein is a process for preparing at least one compound of formula VI,

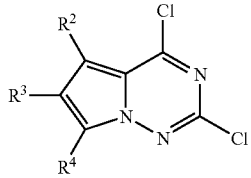

or a pharmaceutically acceptable salt thereof, wherein $R^2$, $R^3$, and $R^4$ are independently selected from H, alkyl, substituted alkyl, hydroxy, alkoxy, halogen, haloalkyl, haloalkoxy, alkanoyl, substituted alkanoyl, amino, substituted amino, aminoalkyl, substituted aminoalkyl, alkylamino, substituted alkylamino, amide, substituted amide, carbamate, ureido, cyano, sulfonamide, substituted sulfonamide, alkylsulfone, cycloalkyl, substituted cycloalkyl, nitro, thio, thioalkyl, alkylthio, disubstituted amino, alkylsulfonyl, alkylsulfinyl, carboxy, alkoxycarbonyl, alkylcarbonyloxy, carbamoyl, —NR$^5$(C═O)R$^6$, alkenyl, substituted alkenyl, alkynyl, substituted alkynyl, and alkylcarbonyl; $R^5$ is H, lower alkyl, or substituted lower alkyl; and $R^6$ is H, alkyl, substituted alkyl, alkoxy, aminoalkyl, substituted aminoalkyl, alkylamino, substituted alkylamino, aryl, or substituted aryl by contacting at least one compound of formula V,

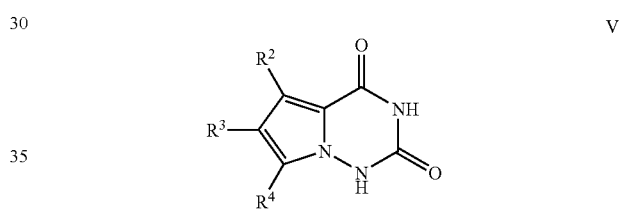

or a pharmaceutically acceptable salt thereof, wherein $R^2$, $R^3$, and $R^4$ are as defined hereinabove, with at least one chlorinating agent to form a mixture, and heating the mixture to form at least one compound of formula VI, or a pharmaceutically acceptable salt thereof.

In one embodiment, $R^2$, $R^3$, and $R^4$ are hydrogen.

A formula V compound, or pharmaceutically acceptable salt thereof can be prepared by contacting at least one compound of formula I,

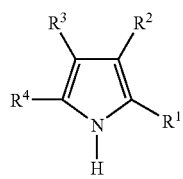

wherein $R^1$ is CHO or CN; $R^2$, $R^3$, and $R^4$ are independently selected from H, alkyl, substituted alkyl, hydroxy, alkoxy, halogen, haloalkyl, haloalkoxy, alkanoyl, substituted alkanoyl, amino, substituted amino, aminoalkyl, substituted aminoalkyl, alkylamino, substituted alkylamino, amide, substituted amide, carbamate, ureido, cyano, sulfonamide, substituted sulfonamide, alkylsulfone, cycloalkyl, substituted cycloalkyl, nitro, thio, thioalkyl, alkylthio, disubstituted amino, alkylsulfonyl, alkylsulfinyl, carboxy, alkoxycarbonyl, alkylcarbonyloxy, carbamoyl, —NR⁵(C=O)R⁶, alkenyl, substituted alkenyl, alkynyl, substituted alkynyl, and alkylcarbonyl; R⁵ is H, lower alkyl, or substituted lower alkyl; and R⁶ is H, alkyl, substituted alkyl, alkoxy, aminoalkyl, substituted aminoalkyl, alkylamino, substituted alkylamino, aryl, or substituted aryl with at least one aminating agent in the presence of at least one base to form at least one compound of formula II,

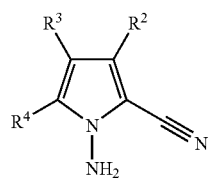
II wherein R², R³, and R⁴ are as defined hereinabove; converting at least one compound of formula II to at least one compound of formula III,

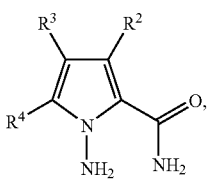
III wherein R², R³, and R⁴ are as defined hereinabove; and contacting the formula III compound with at least one reagent in the presence of at least one base and at least one solvent to form at least one compound of formula V, or a pharmaceutically acceptable salt thereof.

In general, Formula (V) compounds can be prepared in accordance with Scheme 1 and the general knowledge of one skilled in the art. Solvents, aminating agents, bases, temperatures, pressures, and other reaction conditions may readily be selected by one of ordinary skill in the art. Additionally, starting materials, including, such as, for example, reagents, bases, aminating agents, and formula (I) compounds are either commercially available, or may be readily prepared by one of ordinary skill in the art. Solvates (e.g., hydrates) of the compounds of formula (V) can also be prepared in accordance with methods of salvation generally known in the art.

Accordingly, the compounds of formula (V) can be in the free or hydrate form, and can be obtained by methods exemplified in Scheme 1.

Scheme 1

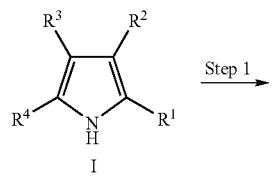

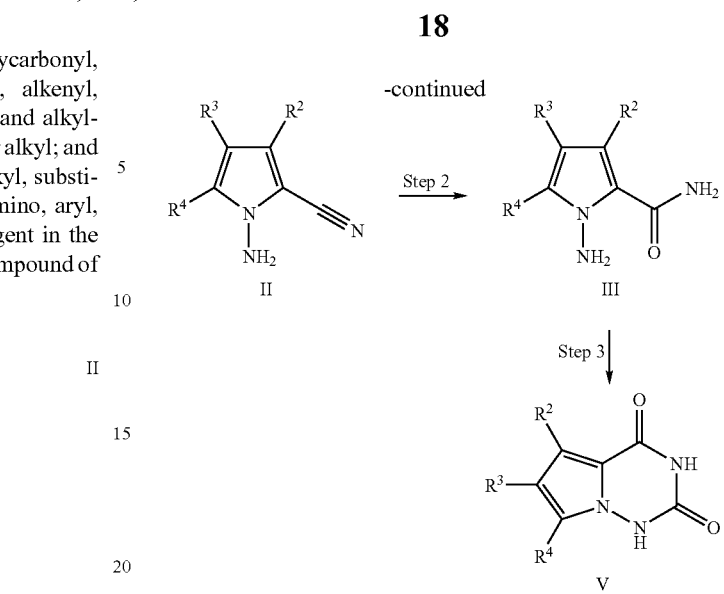

wherein R¹, R², R³, and R⁴ are as defined hereinabove.

Step 1

Compound II can be prepared by contacting an appropriately substituted compound I with an aminating agent, such as for example, hydroxylamino-O-sulfonic acid ($H_2NOSO_3H$) when R¹ is CHO and monochloramine ($NH_2Cl$) when R¹ is CN in the presence of a base, such as, for example, potassium t-butoxide or an aqueous solution of potassium hydroxide. Step 1 can be carried out in accordance with methods readily known to a person of ordinary skill in the art including, but not limited to, for example, the methods disclosed in the Journal of Heterocyclic Chemistry, volume 31, page 781 (1994) and/ or the Journal of Organic Chemistry, volume 69, page 1368 (2004).

Step 2

Compound III can be prepared by converting the nitrile group of compound II to a carboxamide. The nitrile group can be converted to the carboxamide in accordance with any method readily known to a person of ordinary skill in the art. For example, compound II can be contacted with an aqueous solution of a base, such as, for example, potassium hydroxide to partially hydrolyze the nitrile group and form a carboxamide group. An appropriately substituted compound III can be produced in accordance with methods readily known to a person of ordinary skill in the art including, but not limited to, for example, the methods disclosed in the Journal of Heterocyclic Chemistry, volume 31, page 781 (1994) and/or R. C. Larock, Comprehensive Organic Transformations, 2$^{nd}$ edition, page, 1988, Wiley-VCH, New York (1999).

Step 3

Compound V can be prepared by contacting an appropriately substituted compound III with a reagent, such as, for example, ethyl chloroformate in the presence of an appropriate base, such as, for example, pyridine, and a solvent, such as, for example, dioxane. In one embodiment, compound V is produced by heating the mixture of compound III, reagent, base, and solvent at an acceptable temperature and for an acceptable period of time to produce compound V. A person of ordinary skill in the art is readily familiar with and/or able to determine the temperature and period of time at which the mixture of compound III, reagent, base, and solvent may be heated to produce formula V compound.

Exemplary chlorinating agents include, but are not limited to, phosphorous oxychloride, phosphorus pentachloride, and thionyl chloride.

In one embodiment, the chlorinating agent is selected from phosphorous oxychloride, phosphorus pentachloride, and thionyl chloride.

In another embodiment, the chlorinating agent is phosphorous oxychloride.

In yet another embodiment, at least one formula V compound, or a pharmaceutically acceptable salt thereof, is contacted with at least one chlorinating agent in the presence of at least one base and at least one solvent to from a mixture that is then heated to form at least one formula VI compound.

In a further embodiment, at least one formula V compound, or a pharmaceutically acceptable salt thereof, is contacted with at least one chlorinating agent in the presence of at least one base selected from diisopropylethylamine, triethylamine, pyridine, 2,6-lutidine, N,N-dimethylaniline, 4-(dimethylamino)pyridine, and morpholine and at least one solvent to from a mixture that is then heated to form at least one formula VI compound.

In still another embodiment, at least one formula V compound, or a pharmaceutically acceptable salt thereof, is contacted with at least one chlorinating agent in the presence of at least one base and at least one solvent selected from toluene, xylene, and chlorobenzene to from a mixture that is then heated to form at least one formula VI compound.

In an even further embodiment, at least one formula V compound, or a pharmaceutically acceptable salt thereof, is contacted with at least one chlorinating agent selected from phosphorous oxychloride, phosphorus pentachloride, and thionyl chloride in the presence of at least one base and at least one solvent to from a mixture that is then heated to form at least one formula VI compound.

In a still further embodiment, at least one formula V compound, or a pharmaceutically acceptable salt thereof, wherein $R^2$, $R^3$, and $R^4$ are hydrogen is contacted with phosphorous oxychloride in the presence of diisopropylethylamine and toluene to from a mixture that is then heated to form at least one formula VI compound, or a pharmaceutically acceptable salt thereof, wherein $R^2$, $R^3$, and $R^4$ are hydrogen.

A person of ordinary skill in the art is readily familiar with and/or able to determine the temperature and period of time at which the mixture of at least one formula V compound and chlorinating agent may be heated optionally in the presence of base and solvent to produce a compound in accordance with formula VI.

In general, the at least one compound in accordance with formula VI,

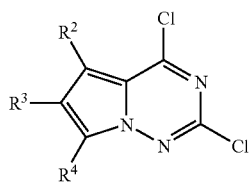

or a pharmaceutically acceptable salt thereof, wherein $R^2$, $R^3$, and $R^4$ are independently selected from H, alkyl, substituted alkyl, hydroxy, alkoxy, halogen, haloalkyl, haloalkoxy, alkanoyl, substituted alkanoyl, amino, substituted amino, aminoalkyl, substituted aminoalkyl, alkylamino, substituted alkylamino, amide, substituted amide, carbamate, ureido, cyano, sulfonamide, substituted sulfonamide, alkylsulfone, cycloalkyl, substituted cycloalkyl, nitro, thio, thioalkyl, alkylthio, disubstituted amino, alkylsulfonyl, alkylsulfinyl, carboxy, alkoxycarbonyl, alkylcarbonyloxy, carbamoyl, —$NR^5$ (C=O)$R^6$, alkenyl, substituted alkenyl, alkynyl, substituted alkynyl, and alkylcarbonyl; $R^5$ is H, lower alkyl, or substituted lower alkyl; and $R^6$ is H, alkyl, substituted alkyl, alkoxy, aminoalkyl, substituted aminoalkyl, alkylamino, substituted alkylamino, aryl, or substituted aryl can be prepared in accordance with Scheme 2 and the general knowledge of one skilled in the art. Chlorinating agents, bases, temperatures, pressures, and other reaction conditions may readily be selected by one of ordinary skill in the art. Additionally, starting materials, including, such as, for example, chlorinating agents and bases, are either commercially available, or may be readily prepared by one of ordinary skill in the art. Tautomers and solvates (e.g., hydrates) of the compounds of formula VI are also within the scope of the invention. Methods of solvation are generally known in the art. Accordingly, the compounds of formula VI can be in the free or hydrate form, and can be obtained by methods exemplified in Scheme 2.

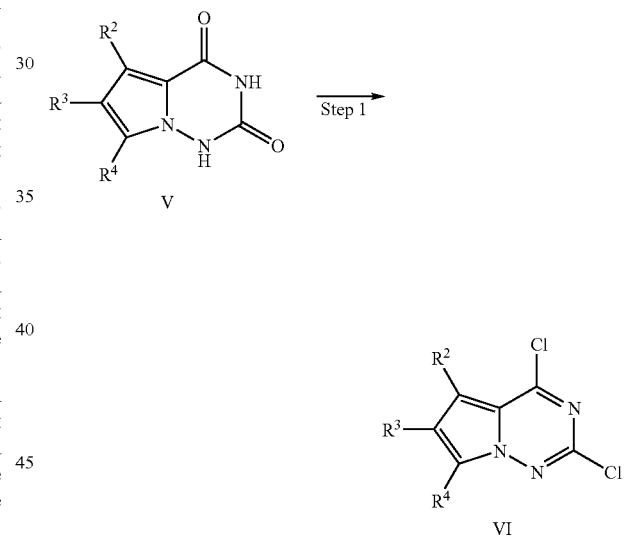

wherein $R^2$, $R^3$, and $R^4$ are as defined hereinabove.

Step 1

Compound VI can be prepared by heating the appropriately substituted compound V with a chlorinating agent, such as, for example, phosphorus oxychloride in the presence of a base, such as, for example, diisopropylethylamine and a solvent, such as, for example, toluene. A person of ordinary skill in the art is readily familiar with and/or able to determine the temperature and period of time at which compound V and chlorinating agent may be heated in the presence of base and solvent to produce compound VI.

Even further described herein is a process for preparing at least one compound in accordance with formula VI:

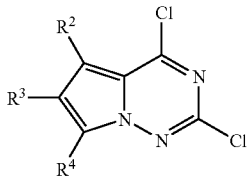

VI

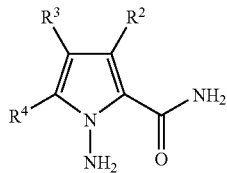

III or a pharmaceutically acceptable salt thereof, wherein $R^2$, $R^3$, and $R^4$ are independently selected from H, alkyl, substituted alkyl, hydroxy, alkoxy, halogen, haloalkyl, haloalkoxy, alkanoyl, substituted alkanoyl, amino, substituted amino, aminoalkyl, substituted aminoalkyl, alkylamino, substituted alkylamino, amide, substituted amide, carbamate, ureido, cyano, sulfonamide, substituted sulfonamide, alkylsulfone, cycloalkyl, substituted cycloalkyl, nitro, thio, thioalkyl, alkylthio, disubstituted amino, alkylsulfonyl, alkylsulfinyl, carboxy, alkoxycarbonyl, alkylcarbonyloxy, carbamoyl, —$NR^5$(C=O)$R^6$, alkenyl, substituted alkenyl, alkynyl, substituted alkynyl, and alkylcarbonyl; $R^5$ is H, lower alkyl, or substituted lower alkyl; and $R^6$ is H, alkyl, substituted alkyl, alkoxy, aminoalkyl, substituted aminoalkyl, alkylamino, substituted alkylamino, aryl, or substituted aryl by contacting at least one compound of formula I,

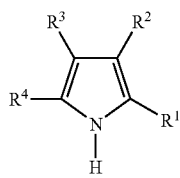

I wherein $R^1$ is CHO or CN and $R^2$, $R^3$, and $R^4$ are as defined hereinabove; with at least one aminating agent in the presence of at least one base to form at least one compound of formula II,

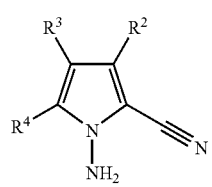

II wherein $R^2$, $R^3$, and $R^4$ are as defined hereinabove; converting at least one compound of formula II to at least one compound of formula III, wherein $R^2$, $R^3$, and $R^4$ are as defined hereinabove; contacting the formula III compound with at least one reagent in the presence of at least one base and at least one solvent to form at least one compound of formula V,

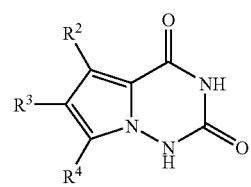

V or a pharmaceutically acceptable salt thereof, wherein $R^2$, $R^3$, and $R^4$ are as defined hereinabove; contacting the formula V compound, or pharmaceutically acceptable salt thereof, with at least one chlorinating agent to form a mixture, and heating the mixture to form at least one compound of formula VI, or a pharmaceutically acceptable salt thereof.

In one embodiment, $R^2$, $R^3$, and $R^4$ are hydrogen.

Exemplary bases that may be used in accordance with the process include, but are not limited to, potassium hydroxide, potassium t-butoxide, pyridine, 2,6-lutidine, N,N-dimethylaniline, 4-(dimethylamino)pyridine, N,N-triethylamine, N,N-diisopropylethylamine, and morpholine.

In another embodiment, the base selected from potassium hydroxide, potassium t-butoxide, pyridine, 2,6-lutidine, N,N-dimethylaniline, 4-(dimethylamino)pyridine, N,N-triethylamine, N,N-diisopropylethylamine, and morpholine.

Exemplary aminating agent that may be used in accordance with the process include, but are not limited to, hydroxylamino-O-sulfonic acid ($H_2NOSO_3H$) and monochloramine ($NH_2Cl$).

In one embodiment, the aminating agent is selected from hydroxylamino-O-sulfonic acid ($H_2NOSO_3H$) and monochloramine ($NH_2Cl$).

In another embodiment, $R^1$ is CHO and the aminating agent is hydroxylamino-O-sulfonic acid.

In a further embodiment, $R^1$ is CN and the aminating agent is monochloramine.

In a still further embodiment, the formula I compound, wherein $R^1$ is CHO, is contacted with hydroxylamino-O-sulfonic acid in the presence of an aqueous solution of potassium hydroxide.

In an even further embodiment, the formula I compound, wherein $R^1$ is CN, is contacted with monochloramine in the presence of potassium t-butoxide.

Exemplary reagents that may be used in accordance with the process include, but are not limited to, for example, methyl chloroformate, ethyl chloroformate, phenyl chloroformate, phosgene, bis(p-nitrophenyl)carbonate, bis(trichloromethyl)carbonate, and 1,1'-carbonyldiimidazole.

In one embodiment, the reagent is selected from methyl chloroformate, ethyl chloroformate, phenyl chloroformate, phosgene, bis(p-nitrophenyl)carbonate, bis(trichloromethyl) carbonate, and 1,1'-carbonyldiimidazole.

In another embodiment, the reagent is ethyl chloroformate.

Exemplary solvents that may be used in accordance with the process include, but are not limited to, dioxane, tetrahydrofuran, diethylether, pyridine, and 1,2-dichloroethane.

In one embodiment, the solvent is selected from dioxane, tetrahydrofuran, diethylether, pyridine, and 1,2-dichloroethane.

In another embodiment, the solvent is dioxane.

The nitrile group of formula II can be converted to the carboxamide of Formula III in accordance with any method readily known to a person of ordinary skill in the art.

In one embodiment, the formula II compound is converted to the formula III compound by contacting the formula II compound with a base.

In another embodiment, the formula II compound is converted to the formula III compound by contacting the formula II compound with a base selected from potassium hydroxide, potassium t-butoxide, pyridine, 2,6-lutidine, N,N-dimethylaniline, 4-(dimethylamino)pyridine, N,N-triethylamine, N,N-diisopropylethylamine, and morpholine.

In a further embodiment, the formula II compound is converted to the formula III compound by contacting the formula II compound with potassium hydroxide.

In one embodiment, the formula III compound is contacted with ethyl chloroformate in the presence of pyridine dioxane to form at least one compound of formula V, or a pharmaceutically acceptable salt thereof.

In another embodiment, the formula III compound is contacted with at least one reagent in the presence of at least one base and at least one solvent to form a mixture that is then heated to form at least one formula V compound, or pharmaceutically acceptable salt thereof.

In a further embodiment, the formula III compound is contacted with at least one reagent selected from methyl chloroformate, ethyl chloroformate, phenyl chloroformate, phosgene, bis(p-nitrophenyl)carbonate, bis(trichloromethyl) carbonate, and 1,1'-carbonyldiimidazole in the presence of at least one base and at least one solvent to form a mixture that is then heated to form at least one formula V compound, or pharmaceutically acceptable salt thereof.

In yet another embodiment, the formula III compound is contacted with at least one reagent in the presence of at least one base selected from potassium hydroxide, potassium t-butoxide, pyridine, 2,6-lutidine, N,N-dimethylaniline, 4-(dimethylamino)pyridine, N,N-triethylamine, N,N-diisopropylethylamine, and morpholine and at least one solvent to form a mixture that is then heated to form at least one formula V compound, or pharmaceutically acceptable salt thereof.

In an even further embodiment, the formula III compound is contacted with at least one reagent in the presence of at least one base and at least one solvent selected from dioxane, tetrahydrofuran, diethylether, pyridine, and 1,2-dichloroethane to form a mixture that is then heated to form at least one formula V compound, or pharmaceutically acceptable salt thereof.

In a still further embodiment, the formula III compound is contacted with at least one reagent selected from methyl chloroformate, ethyl chloroformate, phenyl chloroformate, phosgene, bis(p-nitrophenyl)carbonate, bis(trichloromethyl) carbonate, and 1,1'-carbonyldiimidazole in the presence of at least one base selected from potassium hydroxide, potassium t-butoxide, pyridine, 2,6-lutidine, N,N-dimethylaniline, 4-(dimethylamino)pyridine, N,N-triethylamine, N,N-diisopropylethylamine, and morpholine and at least one solvent selected from dioxane, tetrahydrofuran, diethylether, pyridine, and 1,2-dichloroethane to form a mixture that is then heated to form at least one formula V compound, or pharmaceutically acceptable salt thereof.

In yet a further embodiment, the formula III compound is contacted with ethyl chloroformate in the presence of pyridine and dioxane to form a mixture that is then heated to form at least one formula V compound, or pharmaceutically acceptable salt thereof.

Exemplary chlorinating agents that may be used in accordance with the process include, but are not limited to, phosphorous oxychloride, phosphorus pentachloride, and thionyl chloride In one embodiment, the chlorinating agent is selected from phosphorous oxychloride, phosphorus pentachloride, and thionyl chloride.

In another embodiment, the chlorinating agent is phosphorous oxychloride.

In a further embodiment, at least one formula V compound, or a pharmaceutically acceptable salt thereof, is contacted with at least one chlorinating agent in the presence of at least one base and at least one solvent to from a mixture that is then heated to form at least one formula VI compound.

In an even further embodiment, at least one formula V compound, or a pharmaceutically acceptable salt thereof, is contacted with at least one chlorinating agent in the presence of at least one base selected from diisopropylethylamine, triethylamine, pyridine, 2,6-lutidine, N,N-dimethylaniline, 4-(dimethylamino)pyridine, and morpholine and at least one solvent to from a mixture that is then heated to form at least one formula VI compound.

In still another embodiment, at least one formula V compound, or a pharmaceutically acceptable salt thereof, is contacted with at least one chlorinating agent in the presence of at least one base and at least one solvent selected from toluene, xylene, and chlorobenzene to from a mixture that is then heated to form at least one formula VI compound.

In a still further embodiment, at least one formula V compound, or a pharmaceutically acceptable salt thereof, is contacted with at least one chlorinating agent selected from phosphorous oxychloride, phosphorus pentachloride, and thionyl chloride in the presence of at least one base and at least one solvent to from a mixture that is then heated to form at least one formula VI compound.

In a yet further embodiment, at least one formula V compound, or a pharmaceutically acceptable salt thereof, is contacted with at least one chlorinating agent selected from phosphorous oxychloride, phosphorus pentachloride, and thionyl chloride in the presence of at least one base selected from diisopropylethylamine, triethylamine, pyridine, 2,6-lutidine, N,N-dimethylaniline, 4-(dimethylamino)pyridine, and morpholine and at least one solvent selected from toluene, xylene, and chlorobenzene to from a mixture that is then heated to form at least one formula VI compound.

In a yet still even further embodiment, at least one formula V compound, or a pharmaceutically acceptable salt thereof, is contacted with phosphorous oxychloride in the presence of diisopropylethylamine and toluene to from a mixture that is then heated to form at least one formula VI compound.

In a further embodiment, $R^1$ is CHO; $R^2$, $R^3$, and $R^4$ are H; the aminating agent is hydroxylamino-O-sulfonic acid; the formula II compound is converted to the formula III compound by contacting the formula II compound with potassium hydroxide; the formula V compound is formed by contacting the formula III compound with ethyl chloroformate in the presence of pyridine and dioxane; and the formula VI compound is formed by heating the formula V compound with phosphorus oxychloride in the presence of diisopropylethylamine and toluene.

In an even further embodiment, $R^1$ is CN; $R^2$, $R^3$, and $R^4$ are H; the aminating agent is monochloramine; the formula II compound is converted to the formula III compound by contacting the formula II compound with potassium hydroxide; the formula V compound is formed by contacting the formula III compound with ethyl chloroformate in the presence of pyridine and dioxane; and the formula VI compound is formed by heating the formula V compound with phosphorus oxychloride in the presence of diisopropylethylamine and toluene.

EXAMPLES

The invention is further defined in the following Examples. It should be understood that the Examples are given by way of illustration only. From the above discussion and the Examples, one skilled in the art can ascertain the essential characteristics of the invention, and without departing from the spirit and scope thereof, can make various changes and modifications to adapt the invention to various uses and conditions. As a result, the invention is not limited by the illustrative examples set forth hereinbelow, but rather defined by the claims appended hereto.

All temperatures are in degrees Celsius (° C.) unless indicated otherwise herein.

All reactions were carried out with continuous magnetic stirring under an atmosphere of dry nitrogen or argon. All evaporations and concentrations were carried out on a rotary evaporator under reduced pressure. Commercial reagents were used as received without additional purification. Solvents were commercial anhydrous grades and were used without further drying or purification. Flash chromatography was performed using silica gel (EMerck Kieselgel 60, 0.040-0.060 mm).

The following abbreviations are employed herein: n-BuOH: n-butyl alcohol, $CDCl_3$: chloroform-$^2$H (1), $D_2O$: deuterium oxide, DCM: N-(3,4-dichlorophenyl)-2-methylacrylamide, DMA: dimethylamine, DMF: dimethyl formamide, DMSO: dimethyl sulfoxide, EDC: 1,2-dichloroethane, EtOH: ethanol, HCl: hydrochloric acid, HOAc: acetic acid, IPA: isopropyl alcohol, $K_2CO_3$: potassium carbonate, MeOH: methanol, $MgSO_4$: magnesium sulfate, $NaHCO_3$: sodium bicarbonate, $Na_2SO_4$: sodium sulfate, $NH_4Cl$: ammonium chloride, $NH_3$: ammonia, $N_2$: nitrogen, $POCl_3$: phosphorous oxychloride, THF: tetrahydrofuran, TFA: trifluoroacetic acid, Bn: benzyl, Me: methyl, Et: ethyl, min.: minute(s), h or hr(s): hour(s), L: liter, mL: milliliter, μL: microliter, g: gram(s), mg: milligram(s), mol.: moles, mmol: millimole(s), meq.: milliequivalent, RT or rt: room temperature, ret. t.: HPLC retention time (minutes), sat or sat'd: saturated, aq.: aqueous, TLC: thin layer chromatography, HPLC: high performance liquid chromatography, RP HPLC: reverse phase HPLC, Prep HPLC: preparative reverse phase HPLC, LC/MS: high performance liquid chromatography/mass spectrometry, MS: mass spectrometry, NMR: nuclear magnetic resonance, and mp: melting point.

HPLC Conditions:

In Examples 1-4 the Analytical Reverse Phase HPLC ret. t. was obtained with the column type and length, flow rate, and linear gradient elution identified in each example. Unless indicated otherwise herein, all gradients started with 100% solvent A (MeOH:water:TFA=1:9:0.01) and 0% solvent B, and ended with 100% solvent B (MeOH:water:TFA=1:9:0.01) and 0% solvent A. UV detection was conducted at 220 nm.

Prep. HPLC was performed with a linear gradient elution using $H_2O$/MeOH mixtures buffered with 0.1% trifluoroacetic acid and detection at 220 nm on one of the following columns: Shimadzu S5 ODS-VP 20×100 mm (flow rate=9 mL/min), or YMC S10 ODS 50×500 mm (flow rate=50 mL/min), or YMC S10 ODS 30×500 mm (flow rate=20 mL/min).

All final products were characterized by $^1$H NMR, RP HPLC, electrospray ionization (ESI MS) or atmospheric pressure ionization (API MS) mass spectrometry. $^1$H NMR spectra were obtained on either a 500 MHz JEOL or a 400 MHz Bruker instrument. Field strengths are expressed in units of □ (parts per million, ppm) relative to the solvent peaks, and peak multiplicities are designated as follows: s, singlet; d, doublet; dd, doublet of doublets; dm, doublet of multiplets; t, triplet; q, quartet; br s, broad singlet; m, multiplet.

Example 1

N-[4-({4-[(5-methyl-1H-pyrazol-3-yl)amino]pyrrolo[2,1-f][1,2,4]triazin-2-yl}sulfanyl)phenyl]cyclopropanecarboxamide

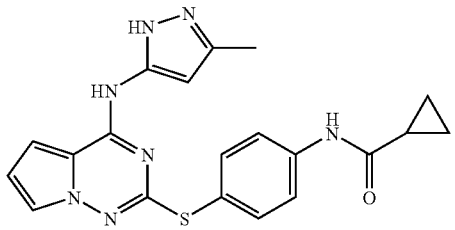

1A. Pyrrolo[2,1-f][1,2,4]triazine-2,4(1H,3H)-dione

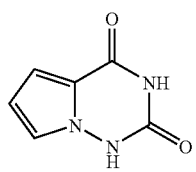

Ethyl chloroformate (4.9 ml, 51 mmol) was added dropwise to a stirred mixture of 1-amino-1H-pyrrole-2-carboxamide (5.85 gm, 46.7 mmol, Journal of Heterocyclic Chemistry, 1994, 31, 781) and dry pyridine (4.2 mL, 51 mmol) in dry dioxane (48 mL) under $N_2$ at RT. The mixture was heated at reflux for 1 hr and then the solvent was removed. The residue was heated at 155° C. for 17 hr and then allowed to cool to RT. The cooled residue was triturated with MeOH. The solid precipitate was collected by filtration and washed with cold MeOH to give 4.43 g 1A (63% yield). $^1$H NMR (DMSO-$d_6$): 6.34 (br. s, 1H), 6.75 (br. s, 1H), 7.12 (br.s, 1H); MS: 152

(M+H)⁺; and RP HPLC ret. t.: 0.36 min (YMC Xterra S7: 3.0×50 mm column, 2 min gradient, 5 mL/min.

1B. 2,4-Dichloropyrrolo[1,2-f][1,2,4]triazine

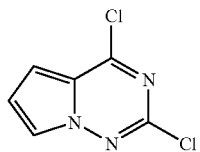

A mixture of 1A (4.7 gm, 31.1 mmol), POCl₃ (8.81 mL, 3 equiv), and diisopropylethylamine (10.8 mL, 2 equiv) in toluene was heated in a pressure vessel at 125° C. for 24 hr. After cooling to RT, the mixture was poured into an ice-cooled sat. aq. solution of NaHCO₃ with stirring. After 10 min, the aq. phase was separated and washed with DCM (3×200 mL). The combined organic phases were washed with brine, dried (Na₂SO₄), and the solvent removed. Silica gel column chromatography (elution with DCM) gave 4.25 g 1B (81% yield) as a yellow solid. ¹H NMR (CDCl₃): 6.96 (m, 1H), 7.03 (m, 1H), 7.85 (m, 1H); MS: 187.9 (M+H)⁺; and RP HPLC ret. t.: 1.63 min. (YMC Xterra S 5:4.6×50 mm column, 2 min gradient, 5 mL/min).

1C. 2-Chloro-N-(5-methyl-1H-pyrazol-3-yl)pyrrolo[1,2-f][1,2,4]triazin-4-amine

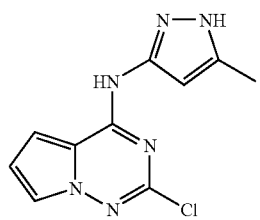

A mixture of 1B (1.50 gm, 8 mmol), 5-methyl-1H-pyrazol-3-amine (801 mg, 1 equiv), and diisopropylethylamine (2.37 mL, 1.7 equiv) in IPA (8 mL) was stirred at RT overnight. MeOH (2 mL) was added and 1.7 g 1C (86% yield) was collected by filtration. ¹HNMR(MeOH-d₄): 2.35 (s, 3H), 6.58 (br. s, 1H), 6.71 (br.s, 1H), 7.02 (br. s, 1H), 7.59 (br.s, 1H); MS: 249 (M+H)⁺; and RP HPLC ret. t.: 1.44 min (Phenomenex-Luna S 10:3.0×50 mm column, 2 min gradient, 4 mL/min).

1D. 2-(4-Aminophenylthio)-N-(5-methyl-1H-pyrazol-3-yl)pyrrolo[1,2-f][1,2,4]triazin-4-amine

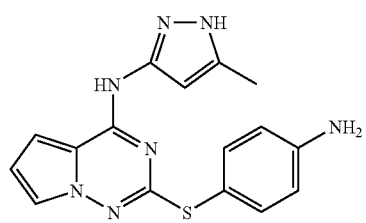

A mixture of 1C (300 mg, 1.21 mmol), 4-aminobenzenethiol (606 mg, 4 equiv) and K₂CO₃ (342 mg, 2 equiv) in dry DMF under a N₂ atmosphere was heated at 120° C. After 1 hr, the mixture was cooled to RT, diluted with 7 mL water, and left stirring for 1 hr. The precipitate was collected by filtration, washed with water and dried. Silica gel column chromatography (step gradient elution with mixtures of DCM containing 0, 2.5, 5, 7.5, 10, 20% MeOH) gave 422 mg 1D as a white solid. ¹H NMR (MeOH-d₄): 2.25 (s, 3H), 5.87 (s, 1H), 6.62 (m, 1H), 6.77 (m, 2H), 6.93 (m, 1H), 7.36 (m, 2H), 7.47 (s, 1H); MS: 338 (M+H)⁺; and RP HPLC ret. t.: 2.04 min (Phenomenex-Luna S 10: 4.6×50 mm column, 3 min gradient, 4 mL/min).

1E. N-[4-({4-[(5-methyl-1H-pyrazol-3-yl)amino]pyrrolo[2,1-f][1,2,4]triazin-2-yl}sulfanyl)phenyl]cyclopropanecarboxamide A solution of cyclopropanecarbonyl chloride (9.1 uL, 0.1 mmol) in dry DCM (0.8 mL) was added to a solution of 1D (33.7 mg, 0.1 mmol) in dry pyridine (0.8 mL) in a vial. The vial was sealed and left stirring over the weekend. Prep. HPLC was used to isolate 13 mg 1E (27% yield) as the TFA salt. ¹H NMR (MeOH-d₄): 0.84 (m, 2H), 0.91 (m, 2H), 1.72 (m, 1H), 2.12 (s, 3H), 5.80 (m, 1H), 6.63 (m, 1H), 7.02 (m, 1H), 7.56 (m, 1H), 7.58 (m, 4H); MS: 406 (M+H)⁺; and RP HPLC ret. t.: 3.23 min (Phenomenex-Luna S10:4.6×50 mm column, 4 min gradient, 4 mL/min).

Example 2

N-(3-cyclopropyl-1H-pyrazol-5-yl)-2-{[3-(methyloxy)phenyl]sulfanyl}pyrrolo[2,1-f][1,2,4]triazin-4-amine

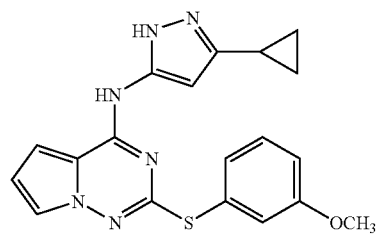

2A. 2-Chloro-N-(5-cyclopropyl-1H-pyrazol-3-yl)pyrrolo[1,2-f][1,2,4]triazin-4-amine

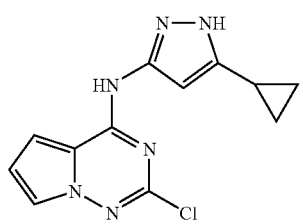

A mixture of 1B (977 mg, 5.2 mmol), 5-cyclopropyl-1H-pyrazol-3-amine (640 mg, 1 equiv), and diisopropylethylamine (1.54 mL, 1.7 equiv) in 5 mL IPA was stirred at RT overnight. The precipitate was collected by filtration to give 1.18 g 2A (83% yield). $^1$H NMR (CDCl$_3$): 0.67 (m, 2H), 0.86 (m, 2H), 1.77 (m, 1H), 6.6 (br. s, 1H), 6.54 (br.s, 1H), 6.79 (br. s, 1H), 7.42 (br.s, 1H); MS: 275 (M+H)$^+$; and RP HPLC ret. t.: 1.56 min (Phenomenex-Luna S10: 3.0×50 mm column, 2 min gradient, 4 mL/min).

2B. N-(3-cyclopropyl-1H-pyrazol-5-yl)-2-{[3-(methyloxy)phenyl]sulfanyl}pyrrolo[2,1-f][1,2,4]triazin-4-amine A mixture of 2A (28 mg, 0.1 mmol), 3-methoxybenzenethiol (61 uL, 5 equiv) and K$_2$CO$_3$ (28 mg, 2 equiv) in dry DMF (0.1 mL) under an N$_2$ atmosphere was heated at 120° C. After 6 hr, the mixture was cooled to RT and applied to a Phenomenex strata-X-C cationic cartridge. The cartridge was subsequently washed with MeOH and a crude product was eluted with a 2 N solution of NH$_3$ in MeOH. The crude product was purified by prep. HPLC to produce 17 mg 2B (44% yield). $^1$H NMR (MeOH-d$_4$): 0.61 (m, 2H), 0.92 (m, 2H), 1.80 (m, 1H), 3.81 (s, 3H), 5.8 (br.s, 1H), 6.63 (m, 1H), 6.94 (m, 1H), 7.01 (br.s, 1H), 7.21 (br.s, 1H), 7.37 (br.s, 1H), 7.49 (s, 1H), 7.75 (s, 1H); MS: 379 (M+H)$^+$; and RP HPLC ret. t.: 1.88 min (Phenomenex-Luna S10:4.6×50 mm column, 3 min gradient, 4 mL/min).

Example 3

N-[4-({4-[(3-cyclopropyl-1H-pyrazol-5-yl)amino]pyrrolo[2,1-f][1,2,4]triazin-2-yl}sulfanyl)phenyl]acetamide

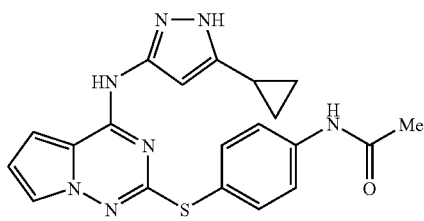

A mixture of 2A (55 mg, 0.2 mmol), N-(4-mercaptophenyl)acetamide (167 mg, 5 equiv) and K$_2$CO$_3$ (55 mg, 2 equiv) in dry DMF (0.1 mL) under an N$_2$ atmosphere was heated at 120° C. After 3 hr, the mixture was cooled to RT, diluted with MeOH, and filtered. Prep. HPLC was used to isolate 53 mg title product (66% yield). $^1$H NMR (MeOH-d$_4$): 0.60 (m, 2H), 0.92 (m, 2H), 1.79 (m, 1H), 2.16 (s, 3H), 5.8 (br.s, 1H), 6.61 (br., 1H), 6.93 (m, 1H), 7.47 (br.s, 1H), 7.57 (m, 2H), 7.71 (m, 2H); MS: 406 (M+H)$^+$; and RP HPLC ret. t.: 1.68 min (Phenomenex-Luna S10: 4.6×50 mm column, 3 min gradient, 4 mL/min).

Example 4

3-({4-[(3-cyclopropyl-1H-pyrazol-5-yl)amino]pyrrolo[2,1-f][1,2,4]triazin-2-yl}sulfanyl)-N-methylbenzamide

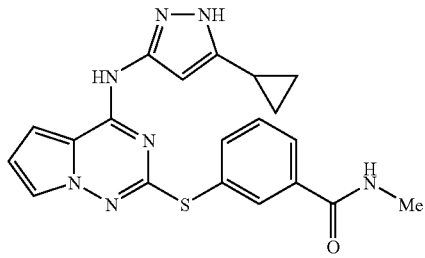

4A. 3-(4-(5-cyclopropyl-1H-pyrazol-3-ylamino)pyrrolo[1,2-f][1,2,4]triazin-2-ylthio)benzoic acid

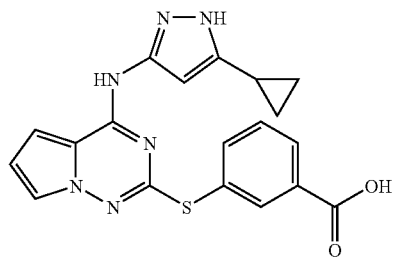

A mixture of 2A (99 mg, 0.36 mmol) and 3-mercaptobenzoic acid (278 mg, 5 equiv) in 1.0 mL n-BuOH was heated in a Smith Synthesizer microwave reactor (Personal Chemistry, Sweden) at 170° C. for 15 hr. After cooling to RT, the mixture was diluted with MeOH, and the precipitate was collected by filtration to give 95 mg 4A (67% yield). $^1$H NMR (DMSO-d$_6$ with a drop of D$_2$O): 0.49 (m, 2H), 0.86 (m, 2H), 1.70 (m, 1H), 5.61 (s, 1H), 6.61 (m, 1H), 7.25 (m, 1H), 7.60 (m, 2H), 7.85 (m, 1H), 8.03 (m, 1H), 8.11 (s, 1H); MS: 393 (M+H)$^+$; and RP HPLC ret. t.: 1.76 min (Phenomenex-Luna S10:4.6×50 mm column, 3 min gradient, 4 mL/min).

4B. 3-({4-[(3-cyclopropyl-1H-pyrazol-5-yl)amino]pyrrolo[2,1-f][1,2,4]triazin-2-yl}sulfanyl)-N-methylbenzamide Methylamine (0.28 mL, 1.4 equiv, 2.0 M solution in THF) followed by EDC (58 mg, 1.5 equiv) were added to a suspension of 4A (78 mg, 0.2 mmol) in dry DCM (0.5 mL) at RT under an N$_2$ atmosphere. After stirring overnight, prep. HPLC was used to isolate 34 mg 4B (43% yield). $^1$H NMR (MeOH-d$_4$): 0.57 (m, 2H), 0.92 (m, 2H), 1.77 (m, 1H), 2.92 (s, 3H), 5.74 (br.s, 1H), 6.62 (br., 1H), 6.94 (br.s, 1H), 7.48 (br.s, 1H), 7.56 (m, 1H), 7.79 (m, 1H), 7.95 (m, 1H), 8.12 (s, 1H); MS: 406 (M+H)$^+$; and RP HPLC ret. t.: 1.63 min (Phenomenex-Luna S10:4.6×50 mm column, 3 min gradient, 4 mL/min).

Example 5

N-(5-methyl-1H-pyrazol-3-yl)-2-(phenylsulfanyl)pyrrolo[2,1-f][1,2,4]triazin-4-amine

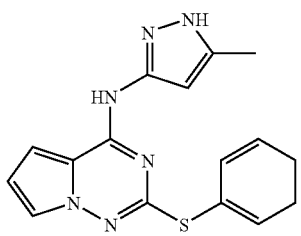

Benzothiophenol (0.1 mL, 2 equiv) was added to suspension of $K_2CO_3$ (151 mg, 2.3 eq.) in 1 mL DMF at rt. After 10 min, 1C (120 mg, 1 eq.) was added as a 3 mL DMF solution. The reaction was stirred at 110° C. overnight, resulting in product formation as shown by LCMS. The reaction was then extracted using ethyl acetate and the combined organic phases washed with water and brine. The organic layer was dried with $MgSO_4$ then concentrated. The crude mixture was triturated with ethyl acetate to obtain the final product. MS: 323 [M+H]$^+$; $^1$H NMR (DMSO-d$_6$): 12.08 (s, 1H), 10.63 (s, 1H), 7.65 (m, 3H); 7.57 (d, 1H), 7.49 (d, 2H), 7.23 (s, 1H), 6.59 (t, 1H), 5.61 (s, 1H), 2.27 (s, 3H).

Example 6

N-(4-((4-((5-methyl-1H-pyrazol-3-yl)amino)pyrrolo[2,1-f][1,2,4]triazin-2-yl)sulfanyl)phenyl)benzamide

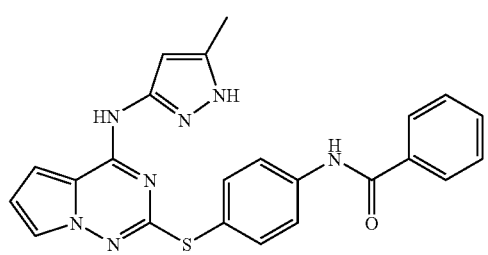

6A. N-(4-Mercapto-phenyl)-benzamide

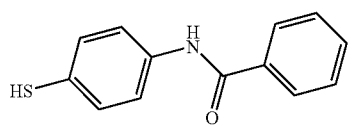

Benzoyl chloride (5.14 mL, 44.28 mL) was added dropwise to a mixture of 4-aminophenol disulfide (5.0 g, 20.13 mmol) and TEA (7.01 mL, 50.3 mmol) in 60 mL DCM at 0° C. The reaction was allowed to stir overnight. The resulting precipitate was collected by filtration. The solid was washed with MeOH and water and then dried. The solid was combined with 200 mL of concentrated HOAc, and 5.0 equiv of zinc powder was added. The reaction was monitored by LCMS. When the reaction was complete, the acetic acid solution was concentrated to approximately 20 mL in volume. The crude mixture was then extracted with water and EtOAc. The organic layer was dried with $MgSO_4$ then concentrated. MS: 228 [M+H]$^+$; $^1$H NMR (DMSO-d$_6$): 10.23 (s, 1H), 7.94 (d, 2H), 7.81 (d, 2H), 7.56 (m, 3H), 7.28 (d, 2H), 5.31 (s, 1H).

6B. N-{4-[4-(5-Methyl-1H-pyrazol-3-ylamino)-pyrrolo[2,1-f][1,2,4]triazin-2-ylsulfanyl]-phenyl}-benzamide 6A (184 mg, 2 equiv) was added to a suspension of $K_2CO_3$ (255 mg, 2.3 equiv) in 5 mL DMF at rt. After 10 min., 1C (100 mg, 1 equiv) was added as a 1 mL DMF solution. The reaction was stirred at 110° C. overnight, resulting in product formation as shown by LCMS. The reaction was then extracted using EtOAc, and the combined organic phases were washed with water and brine. The organic layer was dried with $MgSO_4$ then concentrated. The crude mixture was triturated with EtOAc to obtain 6B. MS: 442 [M+H]$^+$; $^1$HNMR (DMSO-d$_6$): 12.05 (s, 1H), 10.85 (s, 1H), 10.64 (s, 1H), 8.00 (br. m, 5H), 7.45 (br. m, 6H), 7.23 (br. s, 1H), 6.59 (br. s, 1H), 5.8 (br. s, 1H), 2.2 (s, 1H).

We claim:
1. A compound of formula VI,

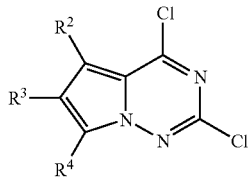

or a pharmaceutically acceptable salt thereof, wherein:
$R^2$, $R^3$, and $R^4$ are H.

2. A process for preparing the compound of formula VI,

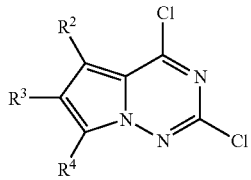

or a pharmaceutically acceptable salt thereof, wherein:
$R^2$, $R^3$, and $R^4$ are H;
comprising:
contacting the compound of formula V,

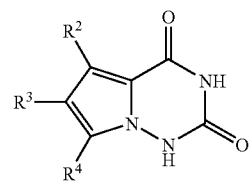

or a pharmaceutically acceptable salt thereof, wherein $R^2$, $R^3$, and $R^4$ are as defined hereinabove, with one or more chlorinating agent to form a mixture, and heating the mixture to form the compound of formula VI, or a pharmaceutically acceptable salt thereof.

3. The process according to claim 2, wherein the formula V compound is contacted with the chlorinating agent in the presence of one or more base and one or more solvent to form the mixture.

4. The process according to claim 3, wherein the chlorinating agent is phosphorous oxychloride; the base is diisopropylethylamine, and the solvent is toluene.

5. The process according to claim 3, wherein the chlorinating agent is selected from phosphorous oxychloride, phosphorus pentachloride, and thionyl chloride.

6. The process according to claim 3, wherein the base is selected from diisopropylethylamine, triethylamine, pyridine, 2,6-lutidine, N,N-dimethylaniline, 4-(dimethylamino)pyridine, and morpholine.

7. The process according to claim 3, wherein the solvent is selected from toluene, xylene, and chlorobenzene.

8. The process according to claim 2, wherein the chlorinating agent is selected from phosphorous oxychloride, phosphorus pentachloride, and thionyl chloride.

9. A process for preparing the compound of formula VI,

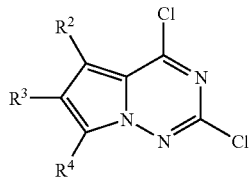

VI or a pharmaceutically acceptable salt thereof, wherein:
$R^2$, $R^3$, and $R^4$ are H;
comprising:
(a) contacting one or more compound of formula I,

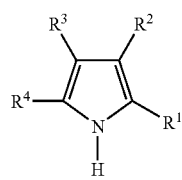

I wherein:
$R^1$ CHO or CN; and
$R^2$, $R^3$, and $R^4$ are as defined hereinabove; with one or more aminating agent in the presence of one or more base to form the compound of formula II,

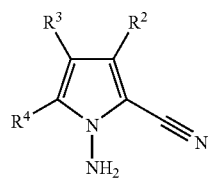

II wherein $R^2$, $R^3$, and $R^4$ are as defined hereinabove;
(b) converting the compound of formula II to the compound of formula III,

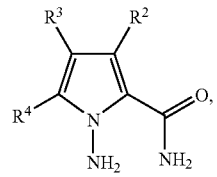

III wherein $R^2$, $R^3$, and $R^4$ are as defined hereinabove; and
(c) contacting the formula III compound with one or more reagent in the presence of one or more base and one or more solvent to form the compound of formula V,

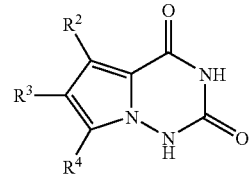

V wherein $R^2$, $R^3$, and $R^4$ are as defined hereinabove, or a pharmaceutically acceptable salt thereof and
(d) contacting the formula V compound with one or more chlorinating agent to form a mixture, and heating the mixture to form the compound of formula VI, or a pharmaceutically acceptable salt thereof.

10. The process according to claim 9, further comprising heating the step (c) mixture of formula III compound, reagent, base, and solvent to form the formula V compound or pharmaceutically acceptable salt thereof.

11. The process according to claim 9, wherein the mixture is formed by contacting the formula V compound with the chlorinating agent in the presence of one or more base and one or more solvent.

12. The process according to claim 11, wherein the chlorinating agent is selected from phosphorous oxychloride, phosphorus pentachloride, and thionyl chloride; the base is selected from diisopropylethylamine, triethylamine, pyridine, 2,6-lutidine, N,N-dimethylaniline, 4-(dimethylamino)pyridine, and morpholine; and the solvent is selected from toluene, xylene, and chlorobenzene.

13. The process according to claim 9, wherein the formula II compound is converted to the formula III compound by contacting the formula II compound with a base.

14. The process according to claim 9, wherein $R^1$ is CHO; $R^2$, $R^3$, and $R^4$ are H; the aminating agent is hydroxylamino-O-sulfonic acid; the formula II compound is converted to the formula III compound by contacting the formula II compound with potassium hydroxide; the formula V compound is formed by contacting the formula III compound with ethyl chloroformate in the presence of pyridine and dioxane; and the formula VI compound is formed by heating the formula V compound with phosphorus oxychloride in the presence of diisopropylethylamine and toluene.

15. The process according to claim 9, wherein $R^1$ is CN; $R^2$, $R^3$, and $R^4$ are H; the aminating agent is monochloramine; the formula II compound is converted to the formula III compound by contacting the formula II compound with potassium hydroxide; the formula V compound is formed by contacting the formula III compound with ethyl chloroformate in the presence of pyridine and dioxane; and the formula VI compound is formed by heating the formula V compound with phosphorus oxychloride in the presence of diisopropylethylamine and toluene.

16. The process according to claim 9 wherein the chlorinating agent is selected from phosphorous oxychloride, phosphorus pentachloride, and thionyl chloride.

17. The process according to claim 9, wherein the aminating agent is selected from hydroxylamino-O-sulfonic acid and monochloramine.

18. The process according to claim 9, wherein the base is selected from potassium hydroxide, potassium t-butoxide, pyridine, 2,6-lutidine, N,N-dimethylaniline, 4-(dimethylamino)pyridine, N,N-triethylamine, N,N-diisopropylethylamine, and morpholine; the solvent is selected from dioxane, tetrahydrofuran, diethylether, pyridine, and 1,2-dichloroethane; and the reagent is selected from methyl chloroformate, ethyl chloroformate, phenyl chloroformate, phosgene, bis(p-nitrophenyl)carbonate, bis(trichloromethyl)carbonate, and 1,1'-carbonyldiimidazole.

* * * * *